(12) United States Patent
Panganiban et al.

(10) Patent No.: US 6,927,023 B2
(45) Date of Patent: Aug. 9, 2005

(54) METHOD OF IDENTIFYING MODULATORS OF HIV-1 VPU AND GAG INTERACTION WITH U BINDING PROTEIN (UBP)

(75) Inventors: Antonito T. Panganiban, Albuquerque, NM (US); Michael A. Callahan, Hamilton, MT (US); Mark A. Handley, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 76 days.

(21) Appl. No.: 10/090,378

(22) Filed: Mar. 4, 2002

(65) Prior Publication Data

US 2002/0115830 A1 Aug. 22, 2002

Related U.S. Application Data

(62) Division of application No. 09/301,978, filed on Apr. 29, 1999, now Pat. No. 6,392,015.
(60) Provisional application No. 60/083,567, filed on Apr. 30, 1998.

(51) Int. Cl.$^7$ ................................................ C12Q 1/70
(52) U.S. Cl. ..................... 435/5; 424/152.1; 424/172.1; 424/185.1; 435/339.1; 530/350
(58) Field of Search ........................... 424/172.1, 152.1, 424/185.1, 192.1; 435/5, 339.1; 530/300, 350

(56) References Cited

PUBLICATIONS

S. Bour, et al., "The–Human Immunodeficiency Virus Type 1 Vpu Protein Specifically Binds to the Cytoplasmic Domain of CD4: Implications for a Mechanism of Degradation" J Virol 69:1510–1520 1995.

M.A. Callahan, et al., "Functional Interaction of Human Immunodeficiency Virus Type 1 Vpu and Gag with a Novel Member of the Tetratricopeptide Repeat Protein Family," J. Virol 72(6):5189–5197 1998.

R.J. Geraghty, et al., "Cell Type–dependence for Vpu Function," J. Med. Primatol. 23:146–150, 1994.

Y.–H. Lee, et al., "The HIV–1 Matrix Domain of Gag is Required for Vpu Respnsiveness During Particle Release," Virology 237:46–55, 1997.

M.S. McBride, et al., "Position Dependence of Functional Hairpins Important for Human Immunodeficiency Virus Type 1 RNA Encapsidation In Vivo," J. Virol. 71(3):2050–2058, 1997.

M.S. McBride, et al., "Efficient Encapsidation of Human Immunodeficiency Virus Type 1 Vectors and Further Characterization of cis Elements Required for Encapsidation," Journal of Virology 71(6):4544–4554 1997.

M.D. Schwartz, et al., "Distinct Functions and Requirements for the Cys–His Boxes of the Human Immunodeficiency Virus Type 1 Nucleocapsid Protein during RNA Encapsidation and Replication." J. Virol. 71(12):9295–9305. 1997.

*Primary Examiner*—Ulrike Winkler
(74) *Attorney, Agent, or Firm*—Quarles & Brady LLP

(57) ABSTRACT

A preparation of U binding protein (Ubp) and a gene sequence encoding Ubp and an anti-Ubp antibody are disclosed. An assay to identify modulators of Ubp/Vpu interaction and Gag/Ubp interaction is also disclosed.

2 Claims, 8 Drawing Sheets

```
  1  TCGGTCGCCTGAGAGGTATCACCTCTTCTGGGCTCAAGATGGACAACAAGAAGAGGCCCTACGCCATCATCCAGTTCCTGCATGACCAGCTCCGGCA
                                  M  D  N  K  K  R  L  A  Y  A  I  I  Q  F  L  H  D  Q  L  R  H>

101  CGGGGGCCTCTCGTCCGATGCCCAGGAGAGCTTGGAAGTCGCCATCCAGTGCCTTGAGACACTGCCGTTTGGGGTGACGGTAGAAGACAGTGACTTGGCGCTC
      G  G  L  S  S  D  A  Q  E  S  L  E  V  A  I  Q  C  L  E  T  A  F  G  V  T  V  E  D  S  D  L  A  L>

201  CCTCAGAGACTCTGCCGGAGATATTTGAAGCGGCTGCCACGGGCAAGGAGATGCCGCAGGACCTGAGGAGCCCGGCCCGAACCCCGCCTTCCGAGGAGACT
      P  Q  T  L  P  E  I  F  E  A  A  A  T  G  K  E  M  P  Q  D  L  R  S  P  A  R  T  P  P  S  E  E  D  S>

301  CAGCAGAGGCAGAGCGCCTCAAAACTGAAGACCGAAGGAAACGAGCAGATGAAAGTTGAAGCTGCCGTGCATTTCTACGGAAAAGCCATCGAGCTCAA
      Q  Q  R  Q  S  L  K  T  E  G  N  E  Q  M  K  V  E  N  F  E  A  A  V  H  F  Y  G  K  A  I  E  L  N>

401  CCCCAGCCAAGCGCCGTCTATTCTGCAACAGACCGCAGCCTACAGCAAACTCGGCAACTACGCAGGCGCGTGGCAGGACTGTGAGCGGGCCATCTGCATT
      P  A  N  V  Y  F  C  N  R  A  A  Y  S  K  L  G  N  Y  A  G  A  V  Q  D  C  E  R  A  I  C  I>

501  GACCCGGCTACAGCAGCAAGGCTACGGCAGGATGGGCCTGGCTTCTCCAGCCTCAACAAGCACGTGGAGGCCGTGGCTTACTACAAGAAGGCTGAAGC
      D  P  A  Y  S  K  A  Y  G  R  M  G  L  A  L  S  S  L  N  K  H  V  E  A  V  A  Y  Y  K  K  A  L  E  L>

601  TGGACCCCGACAACGAGACATACAAGTCCAACCTCAAGATAGCGGAGCTGAAGCTGCGGGAGGCCCCAGCCCCAGATTCAGCAGCTCATGAACTAATGGCTTCGAACATGCTAATGAACAATAATCCCCAGATTCAGCAGCTCATGTCCGGCATGATTTCGGGTGGC
      D  P  D  N  E  T  Y  K  S  N  L  K  I  A  E  L  K  L  R  E  A  P  S  P  T  G  G  V  G  S  F  D  I>

701  CGCCGGCCTGCTGAACCCGGGCTTCATGAGCATGGCTTCAATGGCTTCATGAGCATGGCTTCAAATCTAATGAACAATAATCCCCAGATTCAGCAGCTCATGTCCGGCATGATTTCGGGTGGC
      A  G  L  L  N  N  P  G  F  M  S  M  A  S  N  L  M  N  N  P  Q  I  Q  Q  L  M  S  G  M  I  S  G  G>

801  AACAACCCCTTGGGAACTCCCGGCACCAGCCCCTCGAGCCAGAACGACCTGGCCAGCCTCATCCAGGCGGGCCAGCAGTTGCCAGATGCAGCAGCAGA
      N  N  P  L  G  T  P  G  T  S  P  S  Q  N  D  L  A  S  L  I  Q  A  G  Q  Q  F  A  Q  Q  M  Q  Q  Q  N>
```

FIG. 1A

```
 901 ACCCACAGTTGATAGAGCAGCTCAGGAGTCGGAGTCCAATCCGGAGTCGGAGGAGCAACGAGGACGAGCCCAGCGGCCCAGCAGAGGCCCCAGCAGGAGAGTGACGTGCCTGCTCCCGGTGTGA
      P  E  L  I  E  Q  L  R  S  Q  S  G  V  G  R  P  A  T  T  S  R  S  D  A  A  C  S  R  C  D>
1001 CGGCGTCCTTCCCTGGCCGACCCGAGTTCACGTTCAGCCTTCGTGTCTGCCACTTCCTCCTGTTGACTGCTGAGAGAGAGAGGAGACCTCGACCT
      R  V  L  P  W  P  T  R  R  K  P  S  G  C  L  P  L  P  P  V  G  L  P  E  E  R  G  E  E  R  D  L  G  P>
1101 GCATGTCAAGATGATTTTCCCCTTTTATCTCTGCCCTCCACTCCCTTTTTGTAACTCCCTTACAGCCCCCAGACCCTCTTGAAACGAGAGCCAGC
      A  C  Q  D  G  F  S  P  F  F  I  S  A  L  L  H  S  L  F  V  T  P  L  Q  P  P  D  P  S  *
1201 AAGCTGAGCACAGACCAGCAGCCACTCCCTTCCAGCCCCTCCCTTGAGTGTTTTCTAGAATCCTGAGTGTTTTCTAGAATCCTGGGGTGCTCCCGGGCCGCTCTCA
1301 GAGAAGTGGCAGTTTCACGTTCAGCCTTCCAAAGCCTTTTACAGCCCCCGCCCCATCCCGTGTCTGTCTGCCTGGCTCTGCAGGAAC
1401 TCTCCCGTCTGTGAGAAGCCTCTTTCGAGTCCACTCCCGAGTCGAGACCCTCGTGCCCTCTGCTGTCTCAGCCCCTCGGAAGAGCCTCACCCTCAGCCTGGCTCAGAGAGCCGTCTGGGTG
1501 CGGGCCATGTGTGNTTGCATGAGGAACTCTTAGTGGCAGAGACATGTTGACAGAACAGGGAAGGAGCTGGGACCCCCACCCTTTCTGTCTGGTCCTCGCGACTGCTCCTTCTGT
1601 CATAGGACACAGTTTCGTCATGACCTTCTGTCCCGGTTGGGACGCCTTAGCGCCCCAGGAGCTTACCCTCTGTCTGGGTTCCTGAGGCTGAGGGTTCCTGAGGGCTCTGGGGTTCCTGAGG
1701 GGGGCGACATCATGACCTTCTGTCCCGGTTGGGACGCCTTAGCGCCCCAGGAGCTTACCCTCTGTCTGGGTTCCTGAGGCTGAGGGTTCCTGAGGGCTCTGTCCCTA
1801 CCTGGATGTTCATGGCCGAAAGCACCGAGAGCCGGAGCATCCGGAGCATCCTGGGCCTCGTGGGTTCCTGAGGCTCTGGCCTGTCTGTCTGGCCGTCTGGCCGCCGTGTCC
1901 AAACAGCCACCAGGAAGCACCGGAGCATCCGGAGCATCCTGGGCCTCGTGGGTTCCTGAGGCTCTGGCCTGTCTGTCAGCGACGAACCACGGCGCCGTGTCC
2001 CAGCAGCAGGGTTGTCAGTTGCATGCCCTGCAGTCGAGTGTTCAGTGTTCAGTGTTCAGTGTTCAGAGTTCATCCCGTGTATCGTAGTAGCAGTAGAACG
2101 GGGGCCACCCGGCCCTTGCAGCCCGGTCTGTGCCAAGCCACCCGGGTGACGGTGTGGGAATAAATAGGCGTTGTGA
2201 CCTCAAAAAAAAAAAAAA
```

METHOD OF IDENTIFYING MODULATORS OF HIV-1 VPU AND GAG INTERACTION WITH U BINDING PROTEIN (UBP)

CROSS-REFERENCE TO RELATED APPLICATION

This application is a divisional of U.S. Ser. No. 09/301,978, filed Apr. 29, 1999, issued as U.S. Pat. No. 6,392,015, and also claims the benefit of U.S. Ser. No. 60/083,567, filed Apr. 30, 1998.

STATEMENT REGARDING FEDERALLY SPONSORED RESEARCH AND DEVELOPMENT

This invention was made with United States Government support awarded by the following agencies: NIH AI36174. The United States has certain rights in this invention.

BACKGROUND OF THE INVENTION

Human immunodeficiency virus type 1 (HIV-1) is a member of the lentivirus subfamily of retroviruses. Like all retroviruses, lentiviruses encode the gag, pol, and env genes. However, lentiviruses also contain several accessory genes. The accessory gene vpu, which is unique to HIV-1, encodes viral protein U (Vpu) (44). Vpu is a 16-kDa type I integral membrane phosphoprotein that can form oligomeric structures in vitro and in vivo (32, 43). Indirect immunofluorescence indicates that Vpu localizes predominantly to the Golgi complex (29), but some Vpu is also present in association with the plasma membrane (17). The protein contains a hydrophobic N-terminal domain, which serves as the membrane anchor, and a C-terminal hydrophilic cytoplasmic domain (32).

Vpu plays two roles in HIV-1 replication. First, Vpu promotes the specific degradation of the HIV-1 receptor, CD4, in cell-free systems (8) and in vivo (41, 47). Degradation of CD4 enhances the transport and subsequent processing of the HIV-1 envelope glycoprotein by releasing it from complexes with CD4 that trap both proteins in the ER (28). Direct interaction of Vpu with the cytoplasmic domain of CD4 is required, but not sufficient, for CD4 degradation (4). Mutational analysis indicates that the hydrophilic cytoplasmic domain of Vpu is required for Vpu-mediated CD4 degradation (40). The second function of Vpu is the enhancement of virus particle release (19, 29, 43, 45, 48). The effect of Vpu on virus particle release appears to be mediated from a post-ER compartment (41). Whereas the cytoplasmic domain of Vpu is important for the degradation of CD4, the transmembrane domain of Vpu is sufficient for partial enhancement of virus release (40). Thus, based on both differential intracellular site of action and genetic criteria the bipartite roles of Vpu are mechanistically distinct. The HIV-1 Gag protein is sufficient for immature virus capsid formation, and those capsids are fully competent for Vpu-mediated enhancement of release, indicating that an eventual target of Vpu during particle release is intrinsic to Gag (30).

The identification of host cell proteins that function in HIV replication has provided crucial insight into the intricacies of the biology of HIV-1. The identification of CD4 as the principal virus receptor on T-cells has provided a basic paradigm for virus entry (10). Chemokine receptors are proteins involved in chemotaxis of immune system cells and have been co-opted by HIV-1 to allow entry into host cells in conjunction with CD4 (2, 13). Urokinase-type plasminogen activator, a proteinase involved in tissue invasion by macrophages, binds to and cleaves the HIV-1 envelope glycoprotein gp120 and enhances the infectivity of HIV-1 in macrophages (24). Cyclophilins are proteins that bind to the immunosuppressive drug cyclosporin A (CsA) and are members of the immunophilin superfamily, which includes members that facilitate protein folding (18). Cyclophilins A, B, and C interact with HIV-1 Gag, and cyclophilin A is incorporated into virions (15, 31, 46). The incorporation of cyclophilin A into virus particles is required for an early step in replication between membrane fusion and reverse transcription (5). Furin, a subtilisin-like endoprotease, mediates the cleavage of the HIV-1 envelope glycoprotein precursor gp160 to gp120 and gp41, a process required for virus infectivity (22).

BRIEF SUMMARY OF THE INVENTION

In a preferred embodiment, the present invention is an assay suitable to determine inhibitors or modulators of the Ubp/Vpu interaction. This assay comprises the steps of exposing Vpu and Ubp together in the presence of a candidate inhibitor under conditions in which Vpu and Ubp would normally interact in the absence of the inhibitor. One then determines whether Vpu and Ubp interaction occurs. This assay may be either in vivo or in vitro. A successful inhibitor or compound that alters Vpu-Ubp interaction is an excellent candidate for an HIV therapeutic. Conversely, in some instances an increase in affinity might negatively affect replication.

The present invention is also an assay for determining whether a candidate inhibitor inhibits the interaction between Gag and Ubp. This assay comprises the steps of exposing Ubp and Gag in the presence of a candidate inhibitor under conditions in which Ubp and Gag would interact in the absence of the inhibitor. One then determines whether Gag and Ubp interact. This assay may be either in vivo or in vitro. As with the assay above, successful inhibitors or compounds that affect interaction would make excellent candidates for anti-HIV therapeutics.

In another embodiment the present invention is a preparation of U binding protein (Ubp).

In another embodiment, the preparation is a gene sequence encoding Ubp.

In another embodiment, the preparation is an anti-Ubp antibody. This antibody may be either monoclonal or polyclonal.

It is a feature of the present invention that an assay is provided that provides candidates for HIV therapeutics.

It is another feature of the present invention that a preparation of U-binding protein and a gene sequence encoding U-binding protein is disclosed.

Other features, objects and advantages of the present invention will become apparent after examination of the specification, claims and drawings.

BRIEF DESCRIPTION OF THE SEVERAL VIEWS OF THE DRAWINGS

FIG. 1 shows the sequence of the Ubp coding region and flanking untranslated regions, SEQ ID NO 1 (nucleotides) and SEQ ID NO 2 (protein).

In FIG. 2A a GST-Ubp fusion protein and GST alone were expressed and purified as described in Materials and Methods.

FIG. 4 diagrams a comparison of Ubp with other members of the TPR family. FIG. 4B shows alignment of TPR motifs in Ubp and related proteins, SEQ ID NO 11 (the consensus) and SEQ ID NO 12–29 (the comparisons).

FIG. 5 illustrates the interaction between GST-Ubp and Gag expressed in bacteria and in HeLa cells.

FIG. 6 illustrates the effect of Ubp overexpression on HIV-1 particle release.

DETAILED DESCRIPTION OF THE INVENTION

1. In General

Figure 2A:
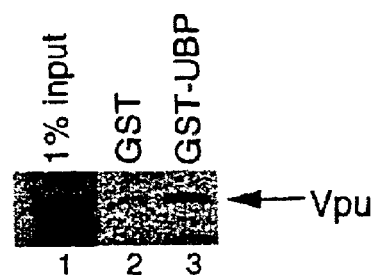
FIGS. 2A and B illustrates interaction between Vpu and Ubp in vitro and in vivo.

Viral protein U (Vpu) is a protein encoded by HIV-1 that promotes the degradation of the virus receptor, CD4, and enhances the release of virus particles from cells.

We isolated a cDNA that encodes a novel cellular protein that interacts with Vpu in vitro, in vivo, and in yeast.

This Vpu-binding protein (Ubp) has a molecular weight of 41-kDa and is expressed ubiquitously in human tissues at the RNA level.

Ubp is a novel member of the tetratricopeptide repeat (TPR) protein family containing four copies of the 34-amino-acid TPR motif. Other proteins that contain TPR motifs include members of the immunophilin superfamily, organelle targeting proteins, and a protein phosphatase.

Ubp also interacts directly with HIV-1 Gag protein, the principal structural component of the viral capsid. However, when Vpu and Gag are coexpressed, stable interaction between Ubp and Gag is diminished. Furthermore, overexpression of Ubp in virus-producing cells resulted in a significant reduction in HIV-1 virion release. Taken together, these data indicate that Ubp plays a role in Vpu-mediated enhancement of particle release.

In one embodiment, the present invention is a preparation of Ubp, a gene sequence encoding Ubp or an antibody specific for Ubp. In another embodiment, the present invention is a method of detecting interaction between either Vpu and Ubp or Gag and Ubp. These methods would be useful to identify inhibitors or modulators of the Vpu/Ubp or Gag/Ubp interaction and, thus, identify potential anti-HIV therapeutics.

2. Ubp and Gene Sequence

In one embodiment, the present invention is a preparation of Ubp. The Examples below describe a method of preparing Ubp involving the isolation of a gene sequence coding Ubp. However, one of skill in the art would know of alternative methods of isolating the protein. For example, one might isolate it from bacterial, baculovirus or mammalian cell preparations.

The present invention is also an anti-Ubp antibody and methods of using anti-Ubp antibodies, such as in detection kits or assays to detect Ubp. This antibody may be either monoclonal or polyclonal. The Examples below describe one Ubp antibody. However, other methods known to those of skill in the art would be equally suitable for antibody preparation.

In another embodiment, the present invention is a gene sequence encoding Ubp. The Examples below, FIG. 1 and SEQ ID NO:1 disclose the sequence of the Ubp coding region as it naturally occurs. The coding region starts at nucleotide 39 and ends at nucleotide 1187.

One may manipulate this gene sequence and still obtain Ubp. For example, one may make nucleotide substitutions without changing the encoded amino acid. Additionally, one may make small mutations, deletions or additions to the protein and still obtain a characteristic Ubp molecule. The Examples below describe the characteristic properties of Ubp.

One may use the Ubp sequence in the following manner:

A. One may generate small peptide derivatives or fragments that affect Vpu-Ubp interaction or Gag-Ubp interaction. These peptides are potential inhibitors.

B. Ubp could be a member of a superfamily of related proteins. Thus, it is likely that other members of such a superfamily could be detected using nucleic acid probes derived from the human Ubp sequence. Other members of the superfamily would likely have functions related to Ubp and could, therefore, be significant.

C. The human Ubp sequence could be used to isolate Ubp homologs from other species. These homologs may have functions that are similar or related to that of human Ubp.

D. Ubp affects particle release of HIV-1. It is possible that Ubp is a component of an export pathway that is common to that of other retroviruses, or even other families of viruses. If so, by interfering with Ubp in cells that are producing other viruses, it might also be possible to interfere with the export of those viruses.

E. Ubp is involved in efficient particle release from cells. It might be possible to use Ubp to enhance the release of particles to increase the titer of HIV vectors or other retrovirus vectors.

The assays described in sections 3 and 4, below, are representative of assays that can be used in the present invention to determine whether a candidate inhibitor has an affect on the interaction between either Vpu and Ubp or Gag and Ubp. Inhibitors or compounds that alter the affinity between Ubp and Vpu or Ubp and Gag would then be excellent candidates for evaluation as anti-HIV therapeutics.

3. Assays to Detect Interaction between Vpu and Ubp

A. In vitro Interaction

Vpu is synthesized in reticulocyte extracts, and Ubp is synthesized in *E. coli* as a fusion protein, such as Ubp-Gst. The two proteins are then incubated together, and the complexes are isolated preferably using glutathione beads (which interact with the Gst portion of the fusion protein). The protein is stripped from the column, and Vpu is then detected by gel electrophoresis.

The principle advantage of this system is that it allows rapid and straightforward examination of mutants and reagents that affect protein-protein interaction.

B. Interaction in Yeast

Vpu is synthesized as a fusion protein, preferably with the DNA binding domain of GAL4, while Ubp is expressed as a fusion protein, preferably with the activation domain of GAL4. When coexpressed in yeast, these two proteins associate with each other by virtue of Vpu-Ubp interaction. This results in the juxtaposition of the GAL4 activation domain with promoters driving indicator genes or selectable markers. Thus, interaction is detected by monitoring the indicator genes or by selection.

This is a viable system for examining the effect of mutants in Vpu or Ubp on Vpu-Ubp interaction. However, it is not as rapid or convenient as the in vitro system.

C. Interaction in vivo

Human cells expressing HIV proteins including Vpu are subjected to lysis. To detect interaction between Vpu and endogenously expressed Ubp, the lysate is then passed through a column containing antibody raised against Ubp. Thus, Ubp is retained on the column and Vpu is also retained by virtue of interaction with Ubp. The protein can then be recovered from the column and Vpu is detected by Western blot analysis with anti-Vpu antiserum.

The main advantage of this system is that the system itself is the normal biologically relevant system. Thus, affects on Vpu-Ubp interaction in the system are highly significant.

4. Assays to Detect Interaction between Gag and Ubp

A. In vitro Interaction

Gag is synthesized in reticulocyte extracts, and Ubp is synthesized in *E. coli* as a fusion protein, such as a Ubp-Gst fusion. The two proteins are then incubated together, and the complexes are isolated using glutathione beads (which interact with the Gst portion of the fusion protein), the protein is stripped from the column. Gag is then detected by Western blot analysis using anti-Gag antibody.

The principle advantage of this system is that it allows rapid and straightforward examination of mutants and, potentially, reagents that affect protein-protein interaction.

B. Interaction in Vivo

Human cells expressing HIV proteins including Gag are subjected to lysis. To detect interaction between Gag and endogenously expressed Ubp, the lysate is then passed through a column containing antibody raised against Ubp. Thus, Ubp is retained on the column and Gag is also retained by virtue of interaction with Ubp. The protein can then be recovered from the column and Gag is detected by Western blot analysis with anti-Gag antiserum.

5. An Assay to Examine the Effect of Ubp on Particle Release

High-level expression of Ubp leads to interference of particle release. We think this is due to competitive interference of Vpu by excess Ubp. This assay would be useful for examining the effect of Vpu, Ubp, and Gag derivatives on particle release itself.

EXAMPLES

1. In General

We used a yeast two-hybrid system to screen a B-lymphocyte cDNA expression library for cellular proteins capable of interacting with Vpu. The principal cDNA that resulted from this screen is a novel cDNA which encodes a 41-kDa protein that is widely expressed on the mRNA level in human tissues. The protein contains four copies of a 34-amino acid repeat motif called the tetratricopeptide repeat (TPR). The TPR family of proteins is composed of proteins of very diverse function including organelle targeting proteins (11, 25), proteins involved in mitosis (26, 42), immunophilins (6, 36), and a nuclear phosphatase (7). Our results indicate that this novel Vpu-binding protein (Ubp) functionally interacts with both Vpu and Gag. Ubp appears to be an intermediary between Vpu and Gag and likely plays a role in virus assembly or release.

2. Materials and Methods

DNA constructions. To construct pKT106, the vpu gene was amplified from pGB107 (16), a derivative of the HIV-1 infectious molecular clone pNL4-3 (1), using the primers vpu1 (5'-AGTAGTACATCATATGCAACCTA-3') (SEQ ID NO:3) and vpu2 (5'-TCCACACAGGATCCCCATAAT-3') (SEQ ID NO:4). The 308-bp amplification product was gel purified and digested with NdeI and BamHI and cloned into the plasmid pAS1-CYH2 (a derivative of pAS1 (12) containing a cycloheximide sensitivity gene) that had also been cut with NdeI and BamHI. pVpui9-1 is a two-hybrid system library plasmid containing the ubp cDNA with a complete 5' end. Sequence analysis of five ubp cDNAs indicated that the cDNA from pVpui9-1 is missing 47 bp of the 3' untranslated region including the polyadenylation signal and the poly-A tail. The sequence in FIG. 1 is derived from the cDNA insert of pVpui9-1 plus the 47 bp of the 3' end from the other cDNAs. pKT173 was constructed by cloning a 1412-bp XhoI-PstI fragment of pVpui9-1 containing the entire ubp coding region into pCITE-2a (Novagen) cut with XhoI and PstI. pKT199, which expresses Vpu in a coupled in vitro transcription/translation system, was created by inserting a 310-bp NdeI-BamHI fragment from pKT106 into pCITE-2a cut with NdeI and BglII. pGEX-Ubp was created by inserting a 2204-bp XhoI fragment from pVpui9-1 into the SalI site of pGEX-4T-1 (Pharmacia). pHIV-Ubp, which expresses Ubp from the HIV-1 LTR, was created by cloning a 1705-bp XhoI-NruI fragment from pVpui9-1 containing the entire ubp coding region into pBG139 (19) that had been cut by SalI and StuI. pJL90 was constructed by amplifying the gag gene from pNL4-3 with the primers 1 (5'-CGGGATCCGGTGCGAGAGCGTCGGTATTAAG-3') (SEQ ID NO:5) and 2 (5'-GCTCTAGACCTGTATCTAATAGAGCTTC-3') (SEQ ID NO:6). The PCR product was gel purified and digested with BamHI and XbaI and inserted into pQE30 (Qiagen) that had been cut with the same two enzymes. pHIVTF (stop), which contains a mutation that creates a premature stop codon immediately following the second amino acid of the transframeshift peptide, was constructed by PR amplification of pMSMΔEnv2 (33) with the sense primer 23233 (5'-GGCCAGATGAGAGAACCAAGG) (SEQ ID NO:7) and the antisense mismatch primer 8264 AflII (5'-CAAAGAGTGACTTAAGGGAAGCTAAAG) (SEQ ID NO:8). A second fragment was derived from the PCR amplification of pMSMΔEnv2 with the antisense primer 23234 (5'-CCTATAGCTTTATGTCCGCAG) (SEQ ID NO:9) and the sense mismatch primer 8265 AflII (5'-CTTTAGCTTCCCTTAAGTCACTCTTTG) (SEQ ID NO:10). These fragments were digested with AflII, ligated, and reamplified with the primers 23233 and 23234. The amplified fragment was digested with SpeI and BclI, and this 922-bp fragment was ligated into pMSMΔEnv2 that had also been digested with SpeI and BclI. pHJ121 was constructed by introducing the SalI-NheI fragment of pBG135 (19) containing the mutated vpu gene into pHIVTF(stop) that had also been cut with SalI and NheI.

Two-hybrid system library screen. The yeast strain Y190 (MATa leu2-3, 112, ura3-52, trp1-901, his3-D200, ade2-101, gal4D gal80D URA3::GAL-lacZ, LYS2::GAL-HIS3, cyh$^r$) was first transformed to Trp prototrophy with pKT106, which expresses Vpu fused to the GAL4 DNA-binding domain. Cells containing this plasmid were grown in Trp-minus synthetic complete (SC) medium and transformed with a human B-lymphocyte cDNA library cloned into a plasmid called pACT (12), which expresses the various cDNA-encoded proteins as hybrids with the GAL4 transcriptional activation domain. Transformations were performed as previously described (39). Doubly-transformed yeast were grown on SC medium lacking His, Leu, and Trp (37) and containing 25 mM 3-amino-1,2,4-triazole (Sigma), and yeast colonies that grew were subjected to an X-gal colony filter assay (12). The cDNA-containing plasmids from His+ colonies that stained blue in the X-gal assay were isolated and tested for their ability to activate transcription alone, and those that did were discarded as false positives. Positive candidate clones were analyzed by restriction digestion and sequencing.

In vitro protein binding assays. For the GST-Ubp/Vpu binding assay, GST and a GST-Ubp fusion protein were expressed in E. coli using the plasmids pGEX-2T and pGEX-Ubp, respectively. The proteins were purified using Glutathione-Sepharose (Pharmacia) according to the manufacturer's directions. Protein concentration was quantified using the Bradford assay (Bio-Rad). Vpu was expressed from the plasmid pKT199 using the TNT rabbit reticulocyte lysate in vitro transcription/translation system (Promega) according to the manufacturer's directions. Reactions were performed in the presence of 23 mCi Tran-35s-label (ICN) to radioactively label the protein. Multiple 25-$\mu$l reactions were performed and pooled after the incubation period. Twenty $\mu$l of pooled Vpu was mixed with 30 pmol of either GST alone or GST-Ubp, and the binding reactions were brought to a total volume of 200 $\mu$l with binding buffer (50–200 mM NaCl, 20 mM Tris-HCl pH 7.9, 1 mM EDTA, 5% glycerol, 0.02% NP-40, 2 $\mu$g/ml leupeptin, 100 $\mu$g/ml PMSF, 0.05% BSA). Binding reactions were incubated on a rocking platform at 4° C. for 2 hours and then at room temperature for 1 hour. A 25-$\mu$l bed volume of Glutathione-Sepharose beads was added to each reaction, and the reactions were incubated for an additional 2 hours at room temperature on a rocking platform. Beads were washed 3× in 1 ml binding buffer and resuspended in 30 $\mu$l standard SDS-PAGE protein sample buffer. Samples were heated in a boiling water bath for 4 minutes, spun at 14,000 rpm in a microcentrifuge for 5 minutes, and loaded onto a SDS/15% polyacrylamide gel.

For the GST-Ubp/Gag interaction assay using Gag expressed in bacteria, his-tagged HIV-1 Gag precursor and a GST-Ubp fusion protein were expressed in E. coli using the plasmids pJL90 and pGEX-Ubp, respectively. Protein was induced from bacterial expression plasmids with isopropyl-b-D-thiogalactopyranoside according to standard methods (38). Bacteria were pelleted 2 hours after induction, washed with TEK buffer (20 mM Tris-HCl, 100 mM KCl, and 1 mM EDTA, pH 7.4) once and then resuspended in lysis buffer (10 mM Tris-HCl, 100 mM KCl, 1 mM EDTA, 5 mM dithiothreitol, 1 mM phenylmethylsulfonyl fluoride, and 0.5% NP-40, pH 7.4). The bacterial pellets were frozen and thawed and sonicated four times for 15 seconds each. Insoluble material was pelleted by centrifugation for 10 minutes in a microfuge at 14 K rpm. Total protein concentrations in the supernatants were determined by the Bradford dye-binding procedure (Bio-Rad). Supernatants were adjusted to 20% glycerol and stored at −80° C. His-tagged Gag protein (approximately 0.1 $\mu$M) was incubated with GST-Ubp fusion protein or GST protein (approximately 0.5 $\mu$M) in 300 $\mu$l Triton buffer (50 mM Tris-HCl, 300 mM NaCl, and 0.5% Triton X-100, pH 7.4) at 4° C. on a rocking platform for one hour. After incubation, a 50-$\mu$l bed volume of Glutathione-Sepharose beads (Pharmacia) was added to each reaction, and the incubation was continued for another half hour. Glutathione-Sepharose beads were pelleted by a 10-second centrifugation in a microfuge and then washed three times with 500 $\mu$l Triton buffer. Washed Glutathione-Sepharose beads were resuspended with 20 $\mu$l 4× protein sample buffer (8% SDS, 50 mM Tris, 40% glycerol, 24.8 mg/ml DTT, 0.4% bromophenol blue, 5% 2-mercaptoethanol, pH 6.8), adjusted to a final volume of 80 $\mu$l, and then heated in a boiling water bath for 5 minutes. After the beads were pelleted in a microfuge, the supernatants were subjected to SDS-PAGE and Western blot analysis using anti-Gag polyclonal antiserum.

For the GST-Ubp/Gag binding assays using Gag expressed in HeLa cells, cells were maintained in Dulbecco's modified Eagle's medium (D-MEM) containing 7% calf serum. One day before transfection, 0.8 million cells were seeded onto 100-mm dishes. HeLa cells were transfected by calcium phosphate coprecipitation followed by glycerol shock with either a vpu+ protease-proviral construct (pHIVTF(stop)) or a vpu$^+$ protease-proviral construct (pHJ121). Forty-eight to sixty hours post-transfection, cells were washed once with phosphate-buffered saline and lysed with 150 $\mu$l Triton lysis buffer (0.5% Triton X-100, 50 mM Tris, 300 mM NaCl, pH 7.5). After incubation on ice for 30 minutes, lysates were spun at 7000 rpm for 6 minutes to pellet cell debris, and supernatants were transferred to new tubes and stored at −20° C. Gag concentrations were determined using a p24 antigen-capture ELISA kit (Coulter). Conditions for the binding assay were the same as those described above for the binding assay with bacterially-expressed Gag protein.

Immunoaffinity column chromatography. An immunoaffinity column was constructed using Affi-Gel 10 (Bio-Rad) and purified IgG from rabbit serum raised against His.Ubp. IgG was coupled to the matrix in coupling buffer (0.1 M HEPES, pH 8.0) at 4° C. for 4 hours, placed in a glass column, and washed extensively with column wash buffer (10 mM sodium phosphate, pH 6.8). HeLa cells were washed 2× with PBS then lysed with cell lysis buffer (50 mM Tris-HCl pH 7.4, 300 mM NaCl, 10 mM iodoacetamide, 0.5% Triton X-100, 0.2 mM PMSF, 0.5 mM leupeptin). Cell lysates were placed on the column by gravity flow, and the column was washed with ten bed volumes of wash buffer. Bound protein was eluted with 100 mM glycine pH 2.5 and 1-ml fractions were collected. Fractions containing protein, determined by O.D. 280 nm, were pooled and concentrated to a 100-$\mu$l volume using Centricon concentrators (Amicon Inc.). These fractions were then analyzed by Western blotting for Ubp and vpu.

Northern blotting. Twenty-five ng of either a 2-kb human b-actin cDNA or the 2204-bp XhoI fragment of pVpui9-1 were labeled with a$^{32}$P-dCTP (Amersham) using a random primed labeling kit (Boehringer Mannheim) according to the manufacturer's directions. Unincorporated nucleotides were removed from the reactions using Sephadex G-50 columns (Boehringer Mannheim). All of the labeled probe from each labeling reaction was used in separate hybridization reactions to probe a multiple human tissue Northern blot (MTN Blot II, Clontech) according to the manufacturer's directions.

Antibody production and purification. Histidine-tagged Ubp, His-tagged HIV-1 Vpu cytoplasmic domain, and His-tagged HIV-1 Gag proteins were expressed in *E. coli* and purified under denaturing conditions with Ni-NTA agarose (Qiagen) according to the manufacturer's directions. The protein samples were dialyzed overnight against 1× PBS. Dialyzed His-tagged proteins were used to raise polyclonal antiserum in rabbits. Crude anti-Gag serum was used for Gag Western blots. IgG was purified from anti-Ubp or anti-Vpu rabbit serum using DEAE Affi-Gel blue (Bio-Rad) or protein-A agarose (Bio-Rad) according to the manufacturer's directions. For Ubp Western blots, anti-Ubp antibodies were further purified with His-Ubp immobilized on Ni-NTA agarose.

Western blotting. For detection of Ubp or Vpu in mammalian cells, cells were lysed in NP-40 lysis buffer (100 mM NaCl, 20 mM Tris pH 7.9, 1 mM EDTA, 0.5% NP-40) and subjected to low-speed centrifugation in a microcentrifuge to remove cellular debris. Cleared cell lysates were mixed with standard SDS-PAGE protein sample buffer and were subjected to electrophoresis on a SDS/15% polyacrylamide gel. Immunoaffinity column samples were electrophoresed on a SDS/10–20% polyacrylamide gradient gel. Proteins were transferred to Immobilon-P membrane (Millipore) using a Mini Trans-Blot electroblotting apparatus (Bio-Rad) in transfer buffer (27.2 mM Tris, 192 mM glycine, 20% methanol) for 2 hours at 150 mA constant current at 4° C. Membranes were blocked overnight in blocking buffer (5% dry milk, 20 mM Tris, 0.01% $NaN_3$). Membranes were then incubated in blocking buffer containing a 1:2000 dilution of an IgG-purified or an antigen affinity-purified rabbit polyclonal Ubp antibody or an IgG-purified rabbit polyclonal Vpu antibody for four hours at room temperature. Membranes were washed 3X in wash buffer (20 mM Tris, 100 mM NaCl, 0.3% Tween-20, 0.005% $NaN_3$) and were subsequently incubated in blocking buffer containing a 1:10,000 dilution of an alkaline phosphatase conjugated goat anti-rabbit IgG (g-chain specific) antibody (Sigma) for two hours at room temperature. Membranes were washed as before and then incubated in 5-bromo-4-chloro-3-indolyl phosphate/nitro blue tetrazolium (BCIP/NBT; Sigma) for 15 minutes at room temperature.

Western blots for luciferase were performed as described above except that a 1:5,000 dilution of an antigen affinity-purified anti-luciferase rabbit polyclonal antibody (Promega) was used for the primary incubation.

For the GST-Ubp/Gag binding assay, proteins from a polyacrylamide gel were transferred to a nitrocellulose membrane using a Trans-Blot Cell electroblotting apparatus (Bio-Rad). The membrane was blocked in blocking buffer (5% dry milk, 3% BSA, in PBS) for 40 minutes and then incubated in PBS containing 5% dry milk and 1% BSA and a 1:200 dilution of a rabbit polyclonal anti-Gag antibody for one hour. The membrane was washed in 1× wash buffer (0.05% Tween-20 in PBS) for 20 minutes and incubated in PBS containing 5% dry milk and 1% BSA and a 1:2500 dilution of a 35S-labeled goat anti-rabbit IgG antibody. Phosphorimage analysis was used for quantitative measurement of Western blots.

DNA sequencing and sequence analysis. Partial sequencing of cDNAs was performed using a Sequenase dideoxy-nucleotide sequencing kit (United States Biochemical). The longest ubp cDNA from pVpui9-1 was sequenced using an automatic sequencing apparatus (Applied Biosystems). Sequence similarity searches of the databases were conducted using the NCBI BLAST e-mail server (3). Exact positions of sequence motifs were determined using the MacVector sequence analysis program (International Biotechnologies) and manual analysis. Sequence identity and similarity was calculated manually or with the Bestfit program from the Wisconsin Genetics Computer Group. p24 antigen-capture ELISA particle release assay. Triplicate cultures of $5 \times 10^5$ HeLa cells were transfected one day after plating by calcium phosphate coprecipitation with one µg of either pGB108 (an env-derivative of the HIV-1 molecular clone NL4-3, (16)) or pBG135 (a vpu– derivative of GB108, (19)) and 14 µg of either pHIV-Ubp or pTAR-luc, a plasmid that expresses firefly luciferase from the HIV-1 LTR. Thirty-six hours after transfection, aliquots of medium were collected and subjected to low-speed centrifugation to remove cell debris, and supernatants were transferred to new tubes. Cells were washed in PBS and scraped into 1 ml PBS and transferred to a centrifuge tube. Cells were pelleted in a microfuge at 6000 rpm for five minutes, and the cell pellets were lysed in 50 µl NETN buffer (0.5% NP-40, 1 mM EDTA, 20 mM Tris pH 8.0, 100 mM NaCl). Lysates were subjected to low-speed centrifugation, and supernatants were transferred to new tubes. The amounts of p24 antigen in medium samples and cell lysates were measured using a p24 antigen-capture ELISA (Coulter Corporation).

3. Results

Interaction between Vpu and a Novel Cellular Protein.

Two lines of evidence are consistent with the interaction between Vpu and one or more cellular factors. Vpu can enhance significantly the release of retrovirus particles as divergent as HIV-2, visna virus, and Moloney murine leukemia virus (21), albeit to a lesser extent than HIV-1 particles. In addition, Vpu-mediated enhancement of virus release is cell-type dependent. Vpu is required for efficient release of virus particles from some cells, such as HeLa cells and CD4+ T-lymphocyte cell lines, but not from other cells, such as COS-1 or CV-1 monkey kidney cells (20) or Balb/c murine lymphoblastoma cells (23).

To identify cellular proteins that might play a role in the activities of Vpu, a yeast two-hybrid system (14) was initially used to screen a human, CD4-negative, lymphocyte cDNA expression library for proteins that interact with Vpu. The two-hybrid system is based on the juxtaposition of the DNA binding and transcriptional activation domains of the yeast transcription factor GAL4. Vpu was expressed as a fusion protein with the GAL4 DNA-binding domain (DBD), and proteins encoded by the cDNA library were expressed as fusions with the GAL4 activation domain. If a particular cDNA-encoded protein interacts with Vpu, then the two domains of GAL4 are brought into close association, and GAL4 function is restored. This causes the activation of two GAL4-responsive reporter genes integrated into the yeast chromosomes: the his3 gene, which confers on the yeast the ability to grow on media lacking histidine, and the *E. coli* lacZ gene, which causes the colonies to stain blue in an X-gal colony filter assay.

1.5 million yeast transformants were screened in the two-hybrid system for interaction with Vpu, and 13 His+, β-gal+ clones were obtained. Ruling out false positives on the basis of activation of transcription in the absence of GAL4-DBD-Vpu and other criteria narrowed these down to five candidate cDNA-expressing plasmids. Partial sequence analysis and restriction enzyme analysis indicated that the five cDNAs contain various lengths of the same sequence. The plasmid containing the longest cDNA, designated pVpui9-1, was also tested in the two-hybrid system with plasmids encoding fusion proteins between the GAL4 DNA-binding domain and two proteins unrelated to Vpu: murine TNF receptor associated factor 2 (TRAF-2) and human ADP ribosylation factor 1 (ARF-1). The protein encoded by the cDNA did not bind to TRAF-2 or ARF-1, indicating that the interaction between Vpu and the protein expressed from pVpui9-1 is specific in yeast (data not shown). FIG. 1 shows the sequence of the ubp coding region and flanking untranslated regions. The complete nucleotide sequence of the longest ubp cDNA obtained from the two-hybrid system Vpu screen is shown with the deduced amino acid sequence of the open reading frame. Numbers to the left of each line designate nucleotide positions. The four TPR motifs are underlined, and the polyadenylation signal is double-underlined.

A search of sequence databases found matches only to partial cDNA sequences of unknown function (accession numbers Z13137 and D58427), indicating that this is a novel cDNA sequence. We have termed this sequence and the protein it encodes Ubp, for Vpu-binding protein. The ubp coding region is 1146 base pairs long, corresponding to a 382-residue protein with a predicted molecular weight of 41.25 kDa. The ubp mRNA contains an exceptionally long 3' untranslated region of 987 base pairs. As discussed in more detail below, Ubp is a member of the tetratricopeptide repeat (TPR) protein family and contains four TPR motifs.

Figure 2B:
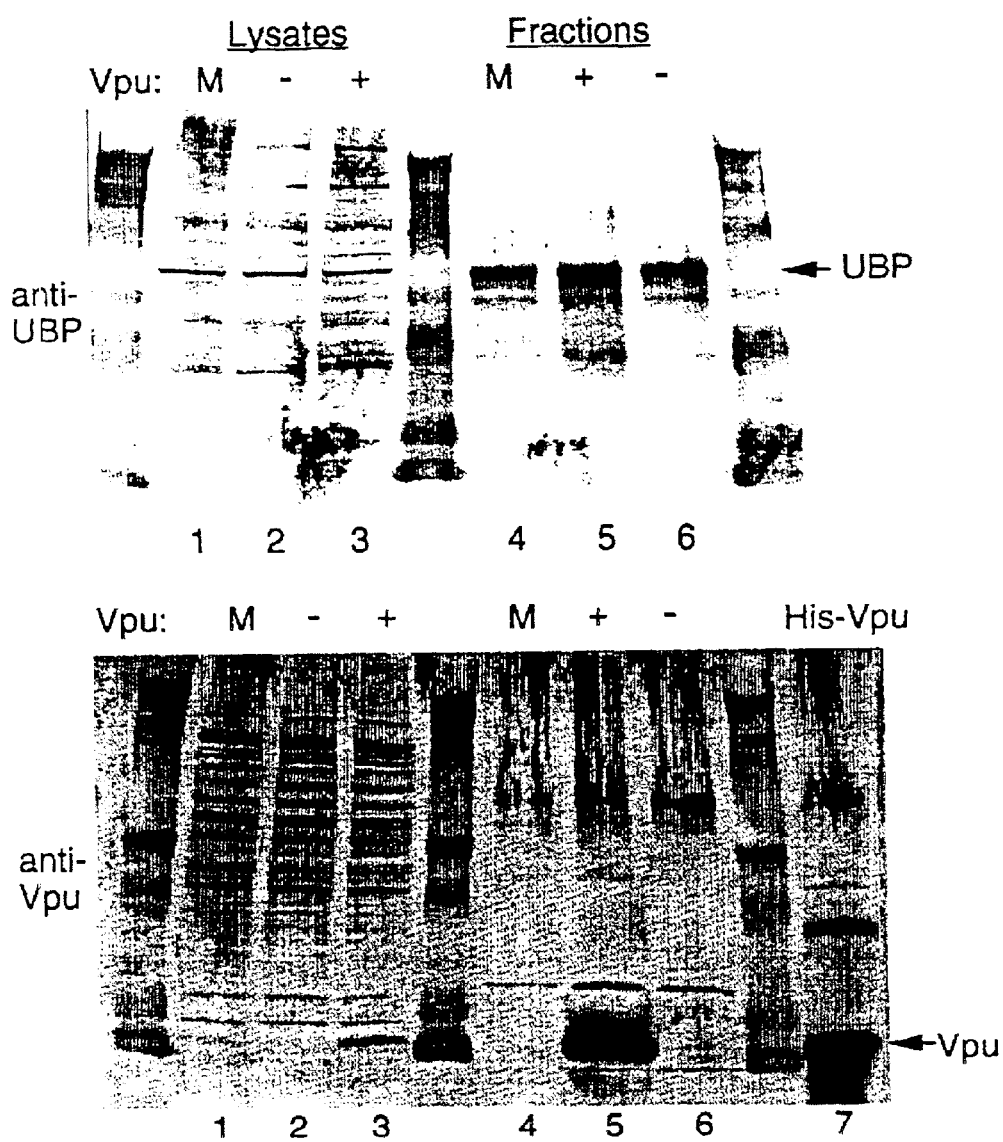
In FIG. 2B lysates of mock-transfected HeLa cells (lane 1) or cells transfected with either a vpu– (pBG135, lane 2) or a vpu+ (pGB108, lane 3) proviral DNA construct were subjected to anti-Ubp immunoaffinity column chromatography analysis as described in Materials and Methods.

To verify the Vpu/Ubp interaction demonstrated with the two-hybrid system, an in vitro binding assay was performed. FIG. 2 illustrates interaction between Vpu and Ubp in vitro and in vivo. In FIG. 2A a GST-Ubp fusion protein and GST alone were expressed and purified as described in Materials and Methods. Protein concentrations were measured using the Bradford assay (Bio-Rad). Equimolar amounts of GST-Ubp (lane 3) or GST alone (lane 2) were incubated in solution with $^{35}$S-labeled in vitro-translated Vpu. GST or GST-Ubp was recovered on Glutathione-Sepharose beads, and Vpu was detected by SDS-PAGE and phosphorimage analysis. Lane 1 shows 1% of the input Vpu used in the binding reactions. In FIG. 2B lysates of mock-transfected HeLa cells (lane 1) or cells transfected with either a vpu− (pBG135, lane 2) or a vpu+ (pGB108, lane 3) proviral DNA construct were subjected to anti-Ubp immunoaffinity column chromatography analysis as described in Materials and Methods. Eluates from immunoaffinity columns are shown in lanes 4–6 (lane 4, mock; lane 5, pGB108; lane 6, pBG135). Cell lysates and column fractions were subjected to Western blot analysis with either anti-Ubp (top panel) or anti-Vpu (bottom panel) antiserum. His-tagged E. coli-expressed Vpu is shown in lane 7.

Ubp was expressed as a fusion protein with a portion of the enzyme glutathione-S-transferase (GST). The GST-Ubp fusion protein was then tested for its ability to bind to in vitro-translated $^{35}$S-labeled Vpu (FIG. 2A). At 75 mM NaCl, Vpu bound to GST-Ubp (lane 3) at a level significantly over the background of GST alone (lane 2) as measured by phosphorimage analysis. The sensitivity of this Vpu-Ubp interaction to salt concentration varied slightly from experiment to experiment, but the highest fold binding over background was always in the range of 50–100 mM NaCl (data not shown).

The binding of Vpu and Ubp was verified in vivo using an immunoaffinity column constructed with the anti-Ubp antibody. pGB108 (16) is an env− derivative of the HIV-1 infectious molecular clone NL4-3. pBG135 (19) is a vpu−derivative of GB108. HeLa cell lysates, representative of mock (lane 1, M), pBG135 (lane 2, Vpu−), or pGB108 (lane 3, Vpu+) transfectants, were placed on the column. Proteins eluted from the column are shown in lanes 4–6 in both panels (lane 4, mock; lane 5, pGB108; lane 6, pBG135). As expected, eluates from all three conditions showed an enrichment for Ubp when analyzed by western blotting (FIG. 2B, top panel, lanes 4–6). When the immunoaffinity column fractions were probed for Vpu, a distinct band appeared in only one lane corresponding to those cells transfected with pGB108 (FIG. 2B, bottom panel, lane 5). Neither Ubp nor Vpu bound to an immunoaffinity column made with preimmune rabbit serum, showing that the purification of Vpu by the anti-Ubp column was due to specific interaction with Ubp (data not shown). These results indicate that Ubp and VPLL stably interact in vivo.

Figure 3A:
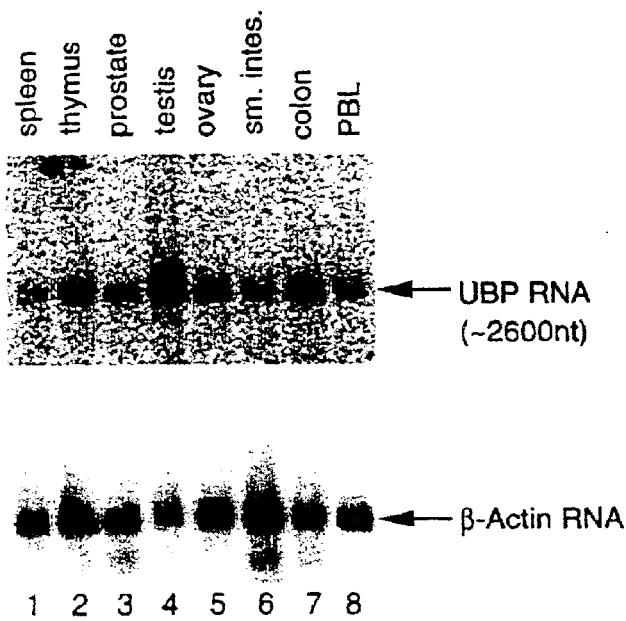
FIG. 3A is a Northern blot analysis of ubp RNA from human cells.
Figure 3B:
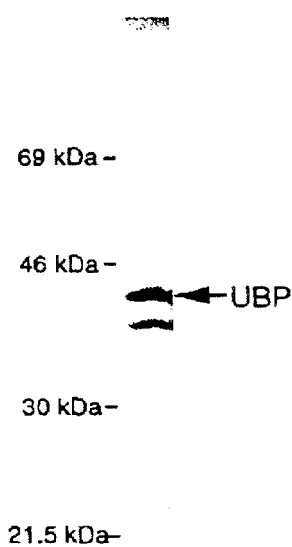
FIG. 3B is an in vitro translation of Ubp. The plasmid KT173 was used to express Ubp in a coupled transcription/translation system (TNT, Promega) in the presence of $^{35}$S-methionine and $^{35}$S-cysteine, and protein was analyzed by SDS-PAGE and detected by phosphorimage analysis.
Figure 3C:
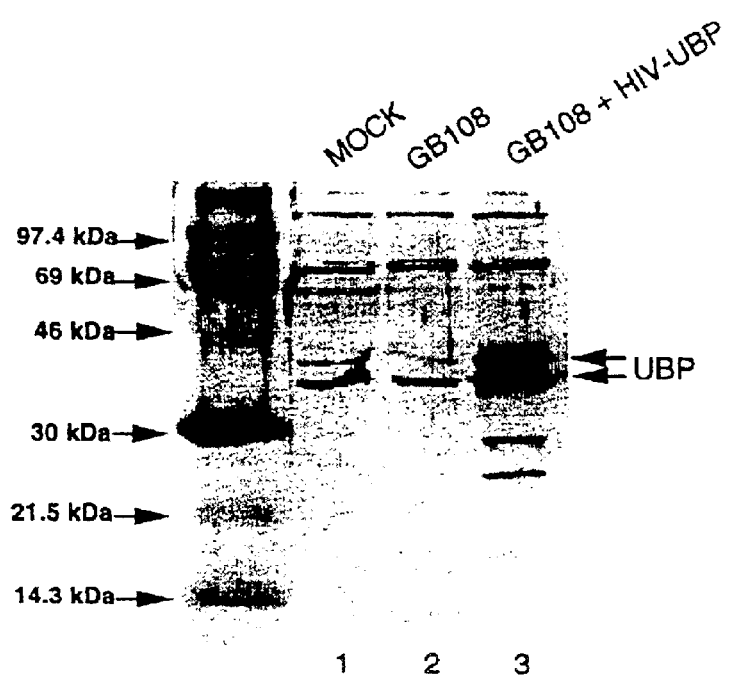
FIG. 3C demonstrates endogenous expression and over-expression of Ubp in HeLa cells.

To identify human cell types that express ubp RNA, we performed Northern blot analysis of RNA from eight human tissues including spleen, thymus, prostate, testis, ovary, colon, small intestine, and peripheral blood leukocytes, using a ubp cDNA probe. FIG. 3A is a Northern blot analysis of ubp RNA from human cells. The top panel shows mRNA from human spleen (lane 1), thymus (lane 2), prostate (lane 3), testis (lane 4), ovary (lane 5), small intestine (lane 6), colon (lane 7), and peripheral blood leukocytes (lane 8), probed with a ubp cDNA probe. The bottom panel shows the same blot when stripped and reprobed with a b-actin control probe. FIG. 3B is an in vitro translation of Ubp. The plasmid KT173 was used to express Ubp in a coupled transcription/translation system (TNT, Promega) in the presence of $^{35}$S-methionine and $^{35}$S-cysteine, and protein was analyzed by SDS-PAGE and detected by phosphorimage analysis. FIG. 3C demonstrates endogenous expression and overexpression of Ubp in HeLa cells. Because high level expression of Ubp from pHIV-Ubp is Tat-dependent, the plasmid pHIV-Ubp was cotransfected with a plasmid that expresses HIV-1 Tat (pGB108 (16)). Lysates of mock-transfected HeLa cells (lane 1), HeLa cells transfected with pGB108 alone (lane 2), and HeLa cells transfected with pHIV-Ubp and pGB108 (lane 3) were subjected to Western blot analysis using an IgG-purified rabbit polyclonal anti-Ubp antibody.

The results of this experiment indicated that ubp RNA is expressed in each of these tissues (FIG. 3A). Moreover, the length of the detected RNA (2600 nt) was consistent with the length of the ubp cDNA (2221 bp) taking into consideration the addition of an average-sized poly-A tail to the ubp mRNA.

To determine whether the ubp open reading frame could be translated to produce a protein of the expected size, we constructed pKT173, a plasmid which expresses the ubp coding region from a phage T7 promoter. pKT173 was used to program in vitro coupled transcription/translation reactions. As shown in FIG. 3B, a protein of about 42 kDa was produced. To ensure that the ubp cDNA contained the entire coding region, we constructed pHIV-Ubp, a plasmid that expresses the ubp cDNA from the HIV-1 LTR. This plasmid was used to overexpress Ubp in HeLa cells. Cells were lysed at forty-eight hours post-transfection, and the lysates were subjected to Western blot analysis with a rabbit polyclonal Ubp antiserum. As shown in FIG. 3C, two Ubp species of slightly different mobility on the gel were produced in cells transfected with pGB108 and pHIV-Ubp (lane 3), and those two species comigrated with two endogenous UBP species in mock-transfected (lane 1) and GB108-transfected (lane 2) cells. Thus, the ubp cDNA appears to contain a full-length open reading frame. Western blot analysis on lysates from COS-1 and CEM (a CD4+ T-cell line) cells indicated that Ubp was also expressed in both of these cell types (data not shown). The genesis of the two species of Ubp in HeLa cells is not clear. The larger of the two species may be the result of post-translational modification. Alternatively, the smaller of the two Ubp species may be a stable degradation or proteolytically processed product of Ubp. In addition, two minor bands of 25 to 28 kDa are detectable in lysates of HIV-Ubp-transfected cells. While the origin of these species is not known, the bands most likely represent degradation products of Ubp. They are more easily detected in HIV-Ubp-transfected cells because of the high level of expression of Ubp.

Figure 4A:
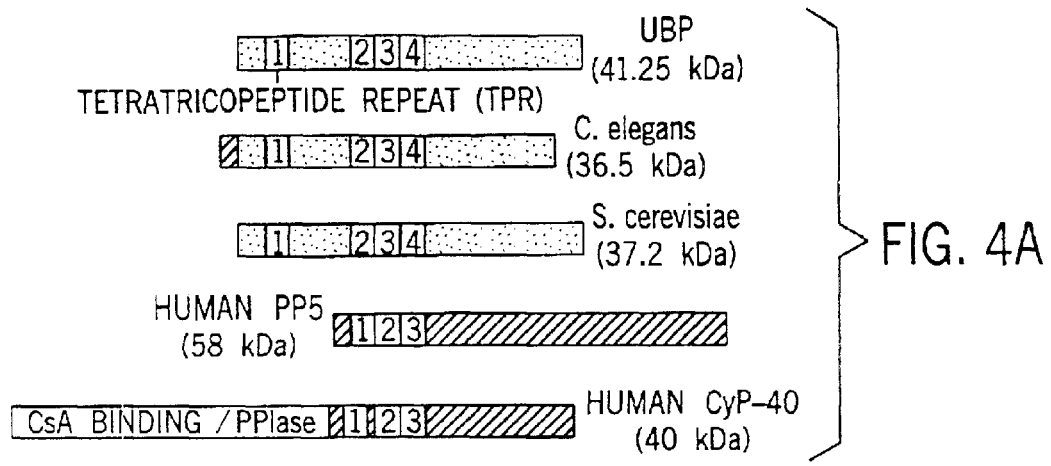
In FIG. 4A Ubp is shown aligned with four proteins resulting from the BLAST sequence similarity search.

Ubp is a Novel Member of the TPR Family of Proteins. The deduced amino acid sequence of Ubp was used to search sequence databases for polypeptides that are similar to Ubp. The results of this search identified a group of very diverse proteins including a protein of unknown function from *C. elegans*, a protein of unknown function from *S. cerevisiae*, two immunophilins (CyP-40 (36) and FKBP59 (6)), two organelle targeting proteins (Pxr1p (11) and MAS70 (25)), a nuclear serine/threonine phosphatase (PP5 (7)), and proteins involved in mitosis (nuc2+ (26) and CDC23 (42)). A comparison of Ubp to four of these proteins is shown in FIG. 4A.

FIG. 4 diagrams a comparison of Ubp with other members of the TPR family. (A) Ubp is shown aligned with four proteins resulting from the BLAST sequence similarity search (3). TPR motifs are shown as numbered white boxes. Regions outside the TPR motifs that show sequence similarity to Ubp are shown in black. Regions that do not contain sequence similarity to Ubp are cross-hatched or shaded. (B) Alignment of TPR motifs in Ubp and related proteins. The amino acid sequences of the TPR motifs of Ubp, *C. elegans* R05F9.10 (accession number U41533), *S. cerevisiae* UNF346 (accession number U43491), human PP5, and human CyP-40, are shown aligned with each other and with the TPR consensus sequence. In the consensus sequence, an asterisk indicates any large hydrophobic residue, and a dash indicates any residue. Sequence identity to Ubp is indicated by black reverse print. Sequence similarity to Ubp is indicated by gray shading.

Figure 4B:
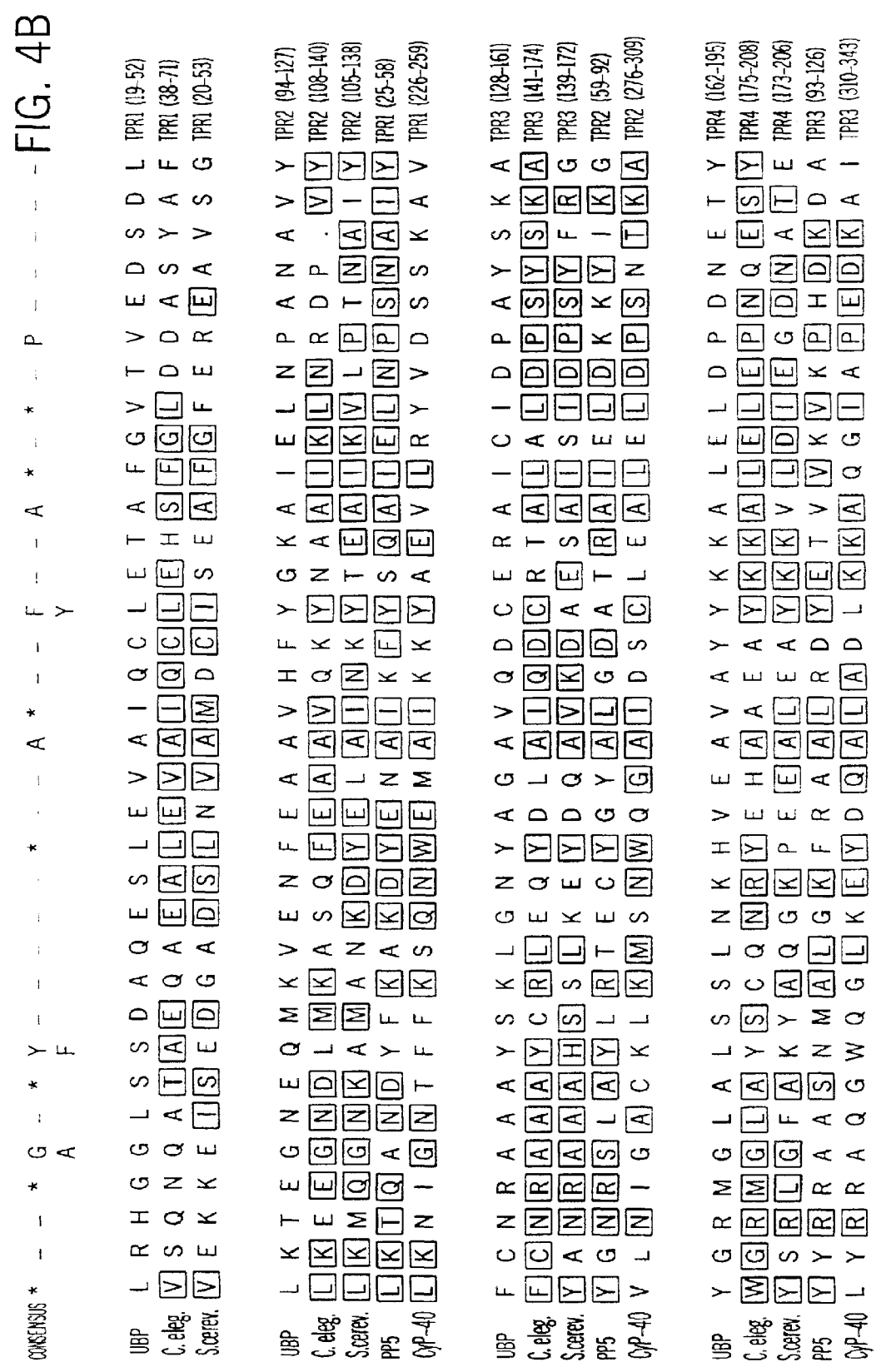

Most of the proteins resulting from the search contain multiple copies of a 34 amino acid long repeat motif called the tetratricopeptide repeat (TPR) (26, 42). Ubp contains four TPR motifs, three of them in tandem (FIG. 1 and FIG. 4A). Similarity between Ubp and most of the proteins identified from the search is almost exclusively limited to the TPR motifs. However, the proteins of unknown function from *C. elegans* and *S. cerevisiae* contain extended regions of similarity to Ubp including sequences outside the TPR motifs, indicating that these proteins are likely to be homologs of human Ubp. The *C. elegans* protein is 45% identical and 63% similar to Ubp with six gaps in the alignment. The *S. cerevisiae* protein is 37% identical and 56% similar to Ubp with eight gaps in the alignment (data not shown). An alignment of the TPR motifs of Ubp with the TPR motifs of other proteins and the TPR consensus sequence (26) is shown in FIG. 4B. The TPR motifs of Ubp match the consensus sequence as well or better than the TPR motifs of previously published TPR proteins.

The TPR family of proteins contains members with very diverse activities, and the motif has been well characterized physically. The TPR motif probably adopts a secondary structure consisting of a 25-30-amino acid amphipathic a-helix followed by a short proline-induced turn. Formation of this structure has been demonstrated by circular dichroism and limited proteolysis for the protein nuc2+ of *S. pombe* (26). These a-helices are believed to interact intra- or intermolecularly with each other through their hydrophobic faces. The TPRs are likely to be involved in mediating interactions between proteins. Indeed, the TPR motifs of the immunophilin FKBP59 (34), the peroxisome targeting protein Pxr1p (11), and a mouse homolog of the nuclear phosphatase PP5 (9) have been shown to be involved in protein-protein interaction.

Interaction Between Ubp and HIV-1 Gag.

The HIV-1 Gag protein is the principal component of the virus particle. Since Gag expression is sufficient for particle formation and responsiveness to Vpu, Gag contains a direct or indirect target of the particle release enhancement activity of Vpu (30). We used multiple approaches to determine whether Vpu and Gag interact directly and have obtained no evidence for such an interaction. However, an alternative possibility is that the ability of Vpu to enhance particle release is manifested through cellular protein intermediates such as Ubp. To determine whether Ubp interacts with Gag, we performed an in vitro binding assay using these two proteins. His-tagged HIV-1 Gag precursor, a GST-Ubp fusion protein, and GST alone were expressed in parallel cultures of *E. coli*, and bacterial lysates were used for the in vitro binding assay. His-tagged Gag was tested for interaction with either GST-Ubp or GST alone.

FIG. 5 illustrates the interaction between GST-Ubp and Gag expressed in bacteria and in HeLa cells. (A) The left panel shows a lysate of *E. coli* expressing His-Gag protein analyzed by Western blot using anti-Gag antiserum. In the right panel, an in vitro binding assay was performed as described in Materials and Methods using His-Gag (the total input is shown in the left panel) and either GST-Ubp (lane 2) or GST alone (lane 1). Gag protein from the binding assay was also detected using Western blot analysis with anti-Gag antiserum. Total protein concentrations of bacterial lysates used in the binding assay were measured by the Bradford assay. (B) The left panel shows anti-Gag Western blot analysis of lysates of HeLa cells transfected with either a vpu− (lane 1) or a vpu+ (lane 2) HIV-1 proviral construct. These lysates were used for in vitro binding assays as described in Materials and Methods, and the results are shown in the right panel (lane 3, vpu− construct; lane 4, vpu+ construct). Gag from HeLa cell lysates did not bind to GST alone (lanes 5 and 6). The presence or absence of Vpu expression in HeLa cells is indicated above the gels.

Figure 5A:
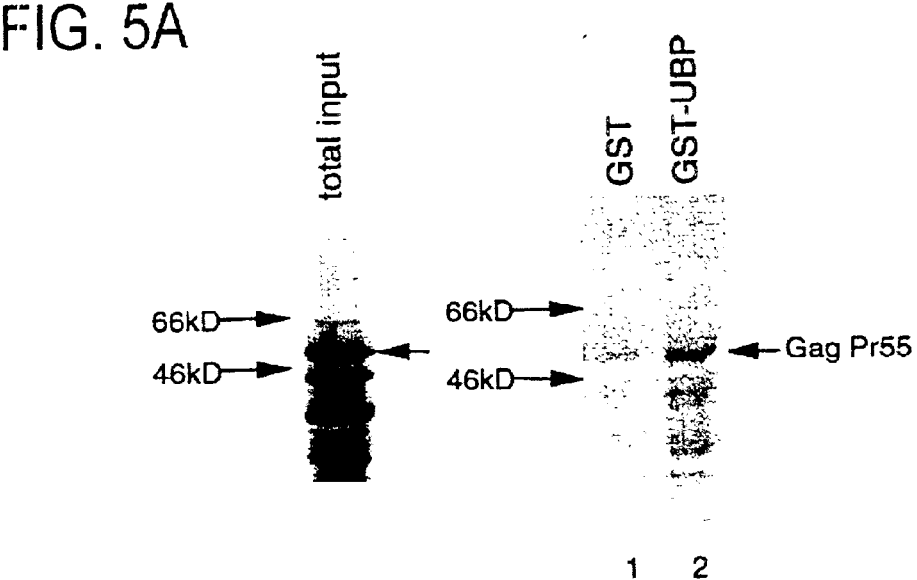
In FIG. 5A the left panel shows a lysate of *E. coli* expressing His-Gag protein analyzed by Western blot using anti-Gag antiserum. In the right panel, an in vitro binding assay was performed as described in Materials and Methods using His-Gag (the total input is shown in the left panel) and either GST-Ubp (lane 2) or GST alone (lane 1).

As shown in FIG. 5A, HIV-1 Gag protein specifically bound to GST-Ubp (lane 2) at a level significantly over the background of GST alone (lane 1) as measured by phosphorimage analysis. The association between Gag and Ubp could be observed at salt concentrations ranging from 1 mM to 500 mM NaCl or KCl (data not shown). A concentration of 300 mM NaCl was found to be optimal for specific binding. In addition, preliminary results with anti-Ubp immunoaffinity column chromatography indicate that Ubp interacts with Gag in HeLa cells (data not shown).

Figure 5B:
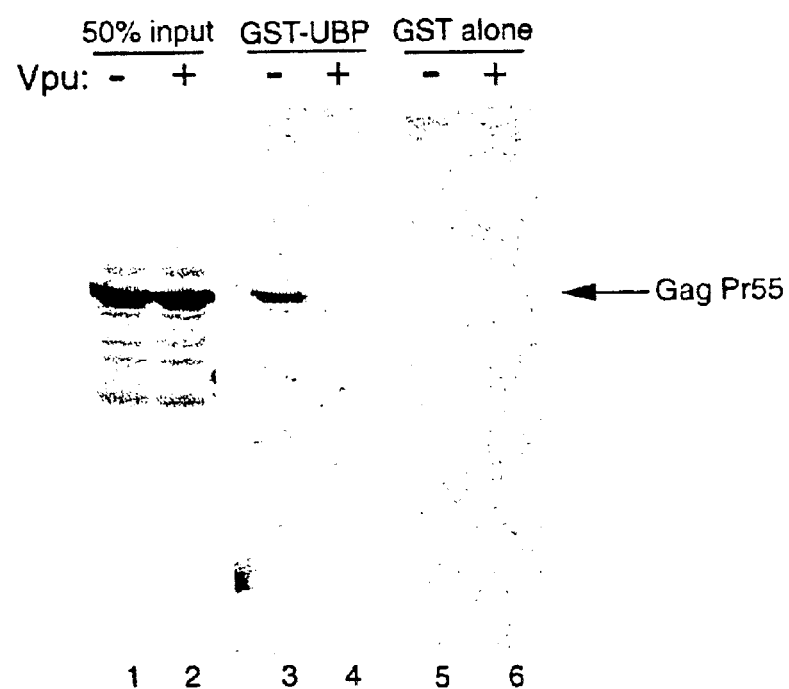
In FIG. 5B the left panel shows anti-Gag Western blot analysis of lysates of HeLa cells transfected with either a vpu– (lane 1) or a vpu$^+$ (lane 2) HIV-1 proviral construct. The results are shown in the right panel of FIG. 5B (lane 3, vpu– construct; lane 4, vpu+ construct).

Gag protein expressed in transfected HeLa cells was also tested for its ability to interact with GST-Ubp. HeLa cells were transfected with either pMS156, a vpu$^+$ protease-HIV-1 proviral construct, or pHJ121, a vpu− protease-proviral construct (30). We examined the efficiency of particle release from cells transfected with these constructs and observed the expected effect: particle release was more efficient in the presence of Vpu (data not shown). Transfected cell lysates were then used as a source of Gag protein for the in vitro binding assay. When Gag was expressed in the absence of Vpu, Gag stably interacted with GST-Ubp (FIG. 5B, lane 3). However, when Gag was expressed in the presence of Vpu, Gag was unable to interact with excess GST-Ubp, indicating that the coexpression of Vpu abrogated stable UBP-Gag interaction (FIG. 5B, lane 4). To see whether Vpu from transfected cells was interacting with GST-Ubp in vitro, thereby preventing interaction between Gag from transfected cells and GST-Ubp, Gag and Vpu were expressed in separate cell cultures, and lysates were mixed and then added to GST-Ubp. The result of this experiment was that Gag was able to bind to GST-Ubp (data not shown). This result demonstrates that Vpu is not simply binding GST-Ubp in vitro and competitively inhibiting interaction between GST-Ubp and Gag. Therefore, the negative effect of Vpu on the ability of Gag to bind Ubp is occurring within HeLa cells. Taken together, these results indicate that Gag may be modified in some way in cells expressing Vpu and that this modification renders Gag unable to interact subsequently with Ubp. It is also worth noting that preliminary results with anti-Ubp immunoaffinity column chromatography indicate that Ubp interacted with Gag in HeLa cells only in the absence of Vpu.

Effect of Ubp Overexpression on HIV-1 Particle Release.

To determine whether Ubp affects Vpu-mediated enhancement of virus release, Ubp was overexpressed in virus-producing cells in the presence and absence of Vpu expression. As a control for non-specific effects of protein overexpression on particle release, luciferase was expressed in cultures that were not overexpressing Ubp. FIG. 6 illustrates the effect of Ubp overexpression on HIV-1 particle release. HeLa cells were mock-transfected (M) or transfected with either pGB108 (lanes 1 and 2, Vpu+) or pBG135 (lanes 3 and 4, Vpu−) and either pHIV-Ubp (lanes 2 and 4, UBP+) or pTAR-luc (lanes 1 and 3, luc+) (27). (A) Thirty-six hours post-transfection, Western blot analysis was performed on cell lysates with antigen affinity-purified . anti-luciferase (top panel) and antigen affinity-purified anti-Ubp (bottom panel) antibodies. Lane numbers above blots correspond to numbers under bar graph in part B. (B) Particle release was assayed using a p24 antigen-capture ELISA as described in Materials and Methods. The data are represented as the ratio of extracellular to intracellular p24 and are normalized to the GB108+TAR-luc cotransfection (bar 1). The data represent one of two independent experiments performed in triplicate. Similar results were obtained from both experiments.

Figure 6B:
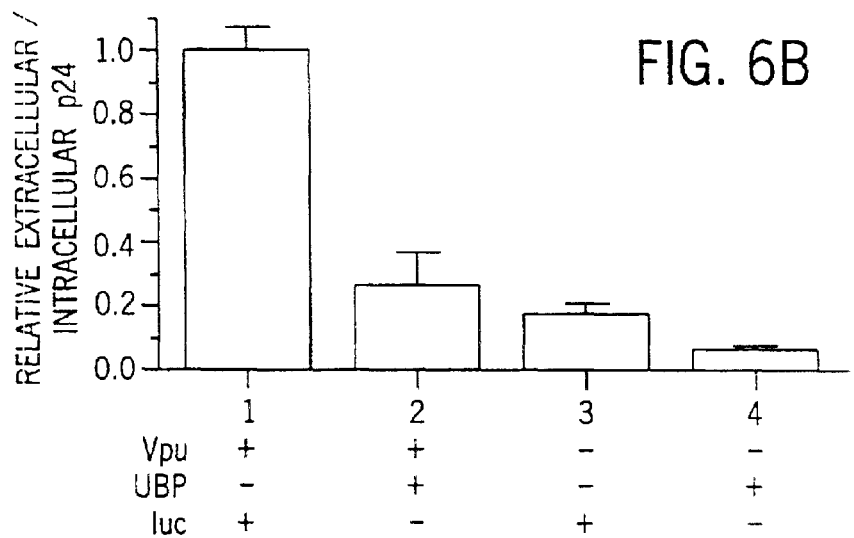
FIG. 6B illustrates a particle release assay using a p24 antigen-capture ELISA as described in Materials and Methods.
Figure 6A:
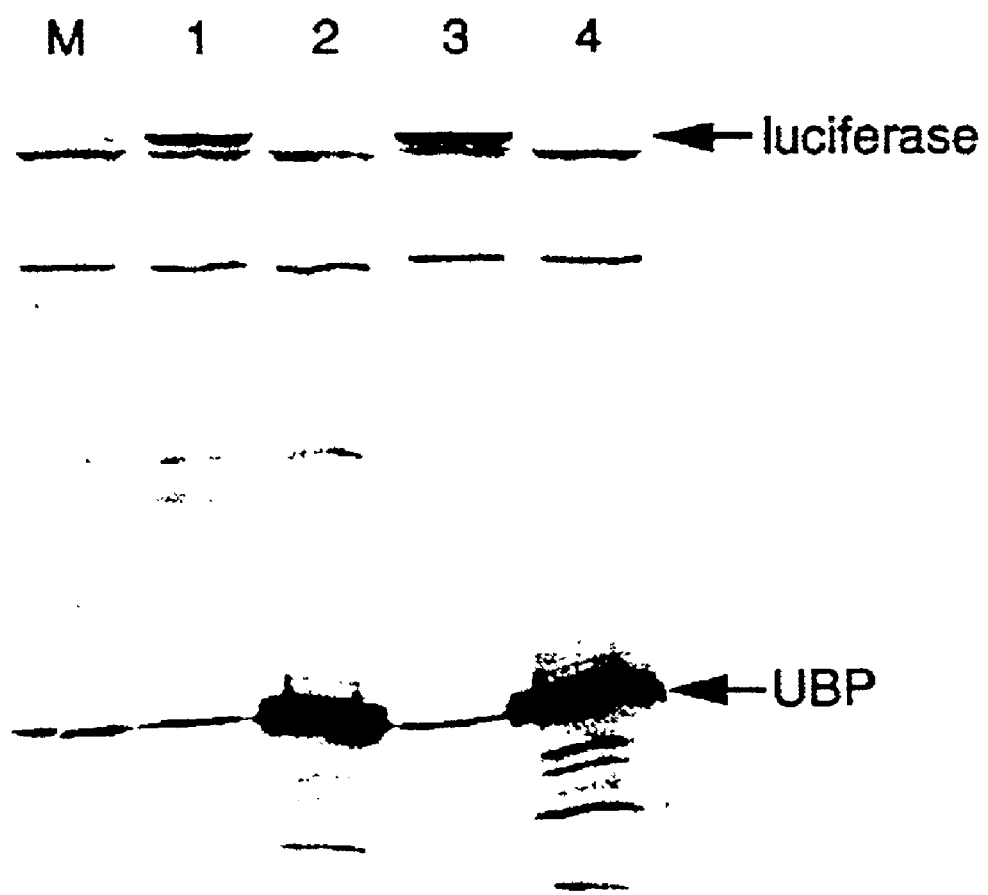
FIG. 6A illustrates a Western blot analysis that was performed on cell lysates with antigen affinity-purified anti-luciferase (top panel) and antigen affinity-purified anti-Ubp (bottom panel) antibodies.

Overexpression of luciferase and Ubp were confirmed by western blot analysis using the appropriate antisera (FIG. 6A). As expected, the lack of wild-type Vpu expression resulted in a five-fold reduction in particle release (FIG. 6B, compare bars 1 and 3). In the presence of Vpu, Ubp overexpression caused a four-fold decrease in virus release (FIG. 6B, compare bars 1 and 2). In the absence of Vpu, particle release was further reduced two- to three-fold by Ubp overexpression (FIG. 6B, compare bars 3 and 4). The intracellular p24 levels in cells overexpressing Ubp were not reduced compared to cells expressing luciferase (data not shown), indicating that the inhibition of particle release by Ubp overexpression was not due to a cytotoxic effect of high levels of Ubp. These results demonstrate that overexpression of Ubp in virus-producing cells has a negative effect on HIV-1 particle release.

4. Discussion

The fact that high level expression of Ubp reduces the efficiency of particle release suggests a simple negative role for Ubp. Moreover, the observation that Vpu forms stable complexes with Ubp and abrogates stable Ubp-Gag interaction is consistent with the idea that association of Ubp with Gag is detrimental to virus release, and that a role of Vpu is to dissociate Ubp-Gag complexes. However, scrutiny of the data from FIG. 5 provides an intriguing alternative possibility. Stable association between Gag and Ubp is detected only in the absence of Vpu; when Vpu is present, only stable Vpu-Ubp complexes are observed. The fact that no detectable Gag is found associated with GST-Ubp when Gag is expressed in the presence of Vpu suggests that the interaction between Ubp and Gag, along with subsequent dissociation by Vpu, leads to an irreversible change in Gag resulting in the inability of Gag to interact with Ubp. In this scenario, Ubp would be a factor required for correct particle formation and release. Overexpression of Ubp would negatively affect particle release simply by competitively inhibiting Vpu: association between excess free Ubp and Vpu would interfere with the ability of Vpu to dissociate Ubp-Gag complexes.

Figure 7:
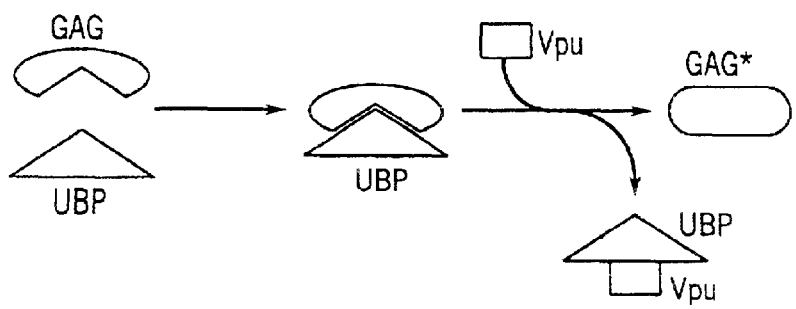
FIG. 7 is a model of the roles of Vpu and Ubp in particle release.

A possible model for Vpu-mediated enhancement of HIV-1 virion release is presented in FIG. 7. FIG. 7 is a model of the roles of Vpu and Ubp in particle release. Ubp interacts with Gag forming a complex. In the absence of Vpu, this complex is stable and may be inhibitory to viral particle release. When Vpu is present, Ubp is disassociated from Gag allowing for modification(s) of Gag to form Gag*. This modification changes the protein in such a way that it can no longer interact with Ubp. Either the inability of Gag* to interact with Ubp or the modification of Gag itself results in enhancement of virus release. Ubp interacts with Gag resulting in the transient formation of Gag-Ubp complexes (in the absence of Vpu, these complexes are stable). Vpu then interacts with Ubp resulting in dissociation of Gag-Ubp complexes. Since the resulting Gag is no longer competent for binding to GST-Ubp, it appears that interaction of Gag with Ubp and subsequent Vpu-mediated dissociation results in an irreversible modification of Gag (in the figure, this modification is indicated by Gag* for heuristic purposes). This uncharacterized modification of Gag may influence Vpu-mediated particle release in one of two ways. First, the conversion of Gag to Gag* may be directly responsible for enhancing particle release in that only particles composed of Gag* can be released efficiently. Alternatively, the modification of Gag may enhance virus release indirectly by rendering Gag* unable to bind to Ubp thereby preventing the formation of inhibitory Gag-Ubp complexes.

Recent experiments indicate that the matrix domain of HIV-1 Gag is required for Vpu-mediated enhancement of particle release (30). Based on these results, we speculate that UBP interacts with the matrix domain of Gag. Preliminary experiments indicate that the interaction of Ubp with Gag may be mediated by the matrix/capsid junction and the p6 domain of Gag (data not shown). The fact that the matrix-capsid junction may be involved in Gag-Ubp interaction raises the possibility that the negative effect of Ubp overexpression on particle release observed in our experiments was due to improper processing of Gag. However, this is unlikely because previous studies have shown that Gag processing does not affect virus release. Moreover, the effect of Vpu on virus particle release can occur in the absence of processing (21, 30). The roles of the matrix domain and Ubp/Gag interaction in Vpu-mediated enhancement of virus release are under investigation.

Ubp contains four tetratricopeptide repeat (TPR) motifs. TPRs are known to form a secondary structure that has been proposed to mediate interaction between two TPRs (26). Therefore, the TPR motifs of Ubp may mediate the interaction of Ubp with Vpu or Gag. Vpu and Gag do not contain TPR motifs. However, the TPRs of FKBP59 (34), Pxr1p (11), and a mouse homolog of PP5 (9) are directly involved in interactions with proteins that do not contain TPRs.

Alternatively, the TPR motifs of Ubp could mediate interaction of Ubp with other cellular proteins involved in the enhancement of virus release. We are currently conducting experiments to identify the domains of Vpu, Gag, and Ubp that account for interactions between Ubp and Vpu or Gag.

The HIV-1 Gag protein interacts with cyclophilins A, B, and C, and cyclophilin A is incorporated into virus particles (15, 31, 46). Cyclophilins and FK506 binding proteins (FKBPs) comprise the immunophilin superfamily. Immunophilins are involved in protein folding, and some act as intracellular receptors for the immunosuppressive drugs CsA and FK506. Ubp is probably not an immunophilin because it lacks an obvious binding site for CsA or FK506. Moreover, Ubp is not detectably incorporated into virus particles (data not shown). However, one possible scenario for Ubp function is that Ubp "modifies" Gag by mediating the proper folding of the protein. The TPR proteins FKBP59 and CyP-40 are known to interact with heat shock protein 90 (hsp90), and these interactions are likely involved in the proper folding of steroid hormone receptors (34, 35).

REFERENCES

1. Adachi, A., H. E. Gendelman, S. Koenig, T. Folks, R. Willey, A. Rabson and M. A. Martin. 1986. Production of acquired immunodeficiency syndrome-associated retrovirus in human and nonhuman cells transfected with an infectious molecular clone. *J. Virol.* 59:284–291.
2. Alkhatib, G., C. Combadiere, C. C. Broder, Y. Feng, P. E. Kennedy, P. M. Murphy and E. A. Berger. 1996. CC CKR5: a RANTES, MIP-1alpha, MIP-1beta receptor as a fusion cofactor for macrophage-tropic HIV-1. *Science.* 272:1955–1958.
3. Altschul, S. F., W. Gish, W. Miller, E. W. Myers and D. J. Lipman. 1990. Basic local alignment search tool. *J. Mol. Biol.* 215:403–10.
4. Bour, S., U. Schubert and K. Strebel. 1995. The human immunodeficiency virus type 1 Vpu protein specifically binds to the cytoplasmic domain of CD4: implications for the mechanism of degradation. *J. Virol.* 69:1510–1520.
5. Braaten, D., E. K. Franke and J. Luban. 1996. Cyclophilin A is required for an early step in the life cycle of human immunodeficiency virus type 1 before the initiation of reverse transcription. *J. Virol.* 70:3551–60.
6. Callebaut, I., J. M. Renoir, M. C. Lebeau, N. Massol, A. Burny, E. E. Baulieu and J. P. Mornon. 1992. An immunophilin that binds Mr 90,000 heat shock protein: main structural features of a mammalian p59 protein. *Proc. Natl. Acad. Sci. USA.* 89: 6270–6274.
7. Chen, M. X., A. E. McPartlin, L. Brown, Y. H. Chen, H. M. Barker and P. T. Cohen. 1994. A novel human protein serine/threonine phosphatase, which possesses four tetratricopeptide repeat motifs and localizes to the nucleus. *EMBO J.* 13:4278–90.
8. Chen, M. Y., F. Maldarelli, M. K. Karczewski, R. L. Willey and K. Strebel. 1993. Human immunodeficiency virus type 1 Vpu protein induces degradation of CD4 in vitro: the cytoplasmic domain of CD4 contributes to Vpu sensitivity. *J. Virol.* 67:3877–84.
9. Chinkers, M. 1994. Targeting of a distinctive protein-serine phosphatase to the protein kinase-like domain of the atrial natriuretic peptide receptor. *Proc. Natl. Acad. Sci. USA.* 91:11075–11079.
10. Daigleish, A. G., P. C. Beverley, P. R. Clapham, D. H. Crawford, M. F. Greaves and R. A. Weiss. 1984. The CD4 (T4) antigen is an essential component of the receptor for the AIDS retrovirus. *Nature.* 312:763–7.
11. Dodt, G., N. Braverman, C. Wong, A. Moser, H. W. Moser, P. Watkins, D. Valle and S. J. Gould. 1995. Mutations in the PTS1 receptor gene, PXR1, define complementation group 2 of the peroxisome biogenesis disorders. *Nat. Genet.* 9:115–125.
12. Durfee, T., K. Becherer, P. -L. Chen, S. -H. Yeh, Y. Yang, A. E. Kilburn, W. -H. Lee and S. J. Elledge. 1993. The retinoblastoma protein associates with the protein phosphatase type 1 catalytic subunit. *Genes & Development.* 7:555–569.
13. Feng, Y., C. Broder, P. E. Kennedy and E. A. Berger. 1996. HIV-1 entry cofactor: functional cDNA cloning of a seven-transmembrane, G protein-coupled receptor. *Science.* 272:872–7.
14. Fields, S. 1993. The two-hybrid system to detect protein-protein interactions. *Methods: A companion to Methods in Enzymology.* 5:116–124.
15. Franke, E. K., H. E. -H. Yuan and J. Luban. 1994. Specific incorporation of cyclophilin A into HIV-1 virions. *Nature.* 372:359–62.
16. Freed, E. O., E. L. Delwart, J. Buchschacher, G. L. and A. T. Panganiban. 1992. A mutation in the human immunodeficiency virus type 1 transmembrane glycoprotein gp41 dominantly interferes with fusion and infectivity. *Proc. Natl. Acad. Sci. USA.* 89:70–74.
17. Friborg, J., A. Ladha, H. Gottlinger, S. Garzon, W. A. Haseltine and E. A. Cohen. 1995. Functional analysis of the phosphorylation sites on the human immunodeficiency virus type 1 Vpu protein. *J. Acquir. Immune. Defic. Syndr.* 8:10–22.
18. Galat, A. 1993. Peptidylproline cis-trans-isomerases: immunophilins. *Europ. J. Biochem.* 216:689–707.
19. Geraghty, R. J. and A. T. Panganiban. 1993. Human immunodeficiency virus type 1 Vpu has a CD4– and an envelope glycoprotein-independent function. *J. Virol.* 67:4190–4.
20. Geraghty, R. J., K. J. Talbot, M. Callahan, W. Harper and A. T. Panganiban. 1994. Cell type-dependence for Vpu function. *J. Med. Primatol.* 23:146–50.
21. Gottlinger, H. G., T. Dorfman, E. A. Cohen and W. A. Haseltine. 1993. Vpu protein of human immunodeficiency virus type 1 enhances the release of capsids produced by gag gene constructs of widely divergent retroviruses. *Proc. Natl. Acad. Sci. USA.* 90:7381–5.
22. Hallenberger, S., V. Bosch, H. Angliker, E. Shaw, H. D. Klenk and W. Garten. 1992. Inhibition of furin-mediated cleavage activation of HIV-1 glycoprotein gp160. *Nature.* 360:358–61.
23. Handley, M. A. unpublished data.
24. Handley, M. A., R. T. Steigbigel and S. A. Morrison. 1996. A role for urokinase-type plasminogen activator in human immunodeficiency virus type 1 infection of macrophages. *J. Virol.* 70:4451–4456.
25. Hase, T., H. Riezman, K. Suda and G. Schatz. 1983. Import of proteins into mitochondria: nucleotide sequence of the gene for a 70-kd protein of the yeast mitochondrial outer membrane. *EMBO J.* 2:2169–2172.
26. Hirano, T., N. Kinoshita, K. Morikawa and M. Yanagida. 1990. Snap helix with knob and hole: essential repeats in S. pombe nuclear protein nuc2+. *Cell.* 60:319–28.
27. Kim, Y. -S. and A. T. Panganiban. 1993. The full-length Tat protein is required for TAR-independent, post-transcriptional trans activation of human immunodeficiency virus type 1 env gene expression. *J. Virol.* 67:3739–3747.
28. Kimura, T., M. Nishikawa and A. Ohyama. 1994. Intracellular membrane traffic of human immunodeficiency virus type 1 envelope glycoproteins: vpu liberates Golgi-targeted gp160 from CD4-dependent retention in the endoplasmic reticulum. *J. Biochem.* 115:1010–20.

29. Klimkait, T., K. Strebel, M. D. Hoggan, M. A. Martin and J. M. Orenstein. 1990. The human immunodeficiency virus type 1-specific protein vpu is required for efficient virus maturation and release. *J. Virol.* 64:621–9.

30. Lee, Y. -H., M. D. Schwartz and A. T. Panganiban. The HIV-1 matrix domain of Gag is required for Vpu responsiveness during particle release. *Virology*. in press.

31. Luban, J., K. L. Bossolt, E. K. Franke, G. V. Kalpana and S. P. Goff. 1993. Human immunodeficiency virus type 1 Gag protein binds to cyclophilins A and B. *Cell.* 73:1067–1078.
32. Maldarelli, F., M. Y. Chen, R. L. Willey and K. Strebel. 1993. Human immunodeficiency virus type 1 Vpu protein is an oligomeric type I integral membrane protein. *J. Virol.* 67:5056–61.
33. McBride, M. S. and A. T. Panganiban. 1996. The human immunodeficiency virus type 1 encapsidation site is a multipartite element composed of functional hairpin structures. *J. Virol.* 70:2963–2973.
34. Radanyi, C., B. Chambraud and E. E. Baulieu. 1994. The ability of the immunophilin FKBP59-HBI to interact with the 90-kDa heat shock protein is encoded by its tetratricopeptide repeat domain. *Proc. Natl. Acad. Sci. USA.* 91:11197–201.
35. Ratajczak, T. and A. Carrello. 1996. Cyclophilin 40 (CyP-40), mapping of its hsp9o binding domain and evidence that FKBP52 competes with CyP-40 for hsp90 binding. *J. Biol. Chem.* 271:2961–2965.
36. Ratajczak, T., A. Carrello, P. J. Mark, B. J. Warner, R. J. Simpson, R. L. Moritz and A. K. House. 1993. The cyclophilin component of the unactivated estrogen receptor contains a tetratricopeptide repeat domain and shares identity with p59 (FKBP59). *J. Biol. Chem.* 268:13187–92.
37. Rose, M. D., F. Winston and P. Hieter. 1990. Methods in yeast genetics. A laboratory course manual. p. 198.
38. Sambrook, J., E. F. Fritsch and T. Maniatis. 1989. Molecular Cloning: A Laboratory Manual. p. 3.
39. Schiestl, R. H. and R. D. Gietz. 1989. High efficiency transformation of intact yeast cells using single stranded nucleic acids as carrier. *Current Genetics.* 16:339–346.
40. Schubert, U., S. Bour, A. V. Ferrer-Montiel, M. Montal, F. Maldarelli and K. Strebel. 1996. The two biological activities of human immunodeficiency virus type 1 Vpu protein involve two separable structural domains. *J. Virol.* 70:809–819.
41. Schubert, U. and K. Strebel. 1994. Differential activities of the human immunodeficiency virus type 1-encoded Vpu protein are regulated by phosphorylation and occur in different cellular compartments. *J. Virol.* 68:2260–71.
42. Sikorski, R. S., M. S. Boguski, M. Goebl and P. Hieter. 1990. A repeating amino acid motif in CDC23 defines a family of proteins and a new relationship among genes required for mitosis and RNA synthesis. *Cell.* 60:307–17.
43. Strebel, K., T. Klimkait, F. Maldarelli and M. A. Martin. 1989. Molecular and biochemical analyses of human immunodeficiency virus type 1 vpu protein. *J. Virol.* 63:3784–91.
44. Strebel, K., T. Klimkait and M. A. Martin. 1988. A novel gene of HIV-1, vpu, and its 16-kilodalton product. *Science.* 241:1221–3.
45. Terwilliger, E. F., E. A. Cohen, Y. C. Lu, J. G. Sodroski and W. A. Haseltine. 1989. Functional role of human immunodeficiency virus type 1 vpu. *Proc. Natl. Acad. Sci. USA.* 86:5163–7.
46. Thali, M., A. Bukovsky, E. Kondo, B. Rosenwirth, C. T. Walsh, J. Sodroski and H. G. Gottlinger. 1994. Functional association of cyclophilin A with HIV-1 virions. *Nature.* 372:363–65.
47. Willey, R. L., F. Maldarelli, M. A. Martin and K. Strebel. 1992. Human immunodeficiency virus type 1 Vpu protein induces rapid degradation of CD4. *J. Virol.* 66:7193–200.
48. Yao, X. J., H. Gottlinger, W. A. Haseltine and E. A. Cohen. 1992. Envelope glycoprotein and CD4 independence of vpu-facilitated human immunodeficiency virus type 1 capsid export. *J. Virol.* 66:5119–26.

We claim:

1. An assay to identify inhibitors of the Ubp/Vpu interaction, comprising the steps of (a) exposing Vpu and Ubp together in the presence of a candidate inhibitor under conditions in which Vpu and Ubp can interact when the inhibitor is not present, wherein Ubp comprises the amino acid sequence of SEQ ID NOs: 12, 15, 20 and 25 and wherein the exposure is in vitro or in a yeast cell, and (b) determining whether Vpu/Ubp interaction occurs, wherein an interaction occurs if a complex of Vpu/Ubp can be isolated or observed.

2. The assay of claim 1 wherein the interaction is measured in vitro.

* * * * *

SEQUENCE LISTING

```
<160> NUMBER OF SEQ ID NOS: 29

<210> SEQ ID NO 1
<211> LENGTH: 2221
<212> TYPE: DNA
<213> ORGANISM: Homo sapiens
<220> FEATURE:
<221> NAME/KEY: unsure
<222> LOCATION: (1514)
<223> OTHER INFORMATION: n =  any nucleotide.
<220> FEATURE:
<221> NAME/KEY: unsure
<222> LOCATION: (2066)
<223> OTHER INFORMATION: n = any nucleotide.

<400> SEQUENCE: 1
tcggtcgcct gagaggtatc acctcttctg ggctcaagat ggacaacaag aagcgcctgg     60
cctacgccat catccagttc ctgcatgacc agctccggca cgggggcctc tcgtccgatg    120
ctcaggagag cttggaagtc gccatccagt gcctggagac tgcgtttggg gtgacggtag    180
aagacagtga ccttgcgctc cctcagactc tgccggagat atttgaagcg gctgccacgg    240
```

-continued

```
gcaaggagat gccgcaggac ctgaggagcc cagcgcgaac cccgccttcc gaggaggact    300
cagcagaggc agagcgcctc aaaaccgaag gaaacgagca gatgaaagtg aaaactttg    360 aagctgccgt gcatttctac ggaaaagcca tcgagctcaa cccagccaac gccgtctatt    420
tctgcaacag agccgcagcc tacagcaaac tcggcaacta cgcaggcgcg gtgcaggact    480
gtgagcgggc catctgcatt gacccggcct acagcaaggc ctacggcagg atgggcctgg    540
cgctctccag cctcaacaag cacgtggagg ccgtggctta ctacaagaag gcgctggagc    600
tggaccccga caacgagaca tacaagtcca acctcaagat agcggagctg aagctgcggg    660
aggcccccag ccccacggga ggcgtgggca gcttcgacat cgccggcctg ctgaacaacc    720
ctggcttcat gagcatggct cgaacctaa tgaacaatcc ccagattcag cagctcatgt    780
ccggcatgat ttcgggtggc aacaacccct gggaactcc cggcaccagc ccctcgcaga    840
acgacctggc cagcctcatc caggcgggcc agcagtttgc ccagcagatg cagcagcaga    900
acccagagtt gatagagcag ctcaggagcc aatccggagt cggacgccca gcgccagcaa    960
cgacgaccag caggagtgac gctgcctgct cccggtgtga ccgcgtcctt ccctggccga    1020
cccgaaggaa gccttctggt tgtctgccac ttcctcctgt tggactgcct gagagagggg    1080
aagagagaga cctcggacct gcatgtcaag atggattttc cccttttatc tctgccctcc    1140
tccactccct ttttgtaact cccttacagc ccccagaccc ttcttgaaac gagagccagc    1200
aagctgagca cagaccagca gcgacctccc ttccagcccc cagaaagctc ggtcacttga    1260
gtgttttcta gaatcctggg gtgctcccgg gccgctctca gagaagtggc aggtttcacg    1320
ttcagccgtg tggcggatcg tgtggcttcc aaagccttt acagcccccg cccccatcc    1380 cgtggtctgt ctgcaggaac tctcccgtct gtgagaagcc tctttccgag tcgacctccc    1440 ggccacccg gccctgtgcc tgctcggaag agctcactgc cagctgcggc ctgggcaccg    1500
cgggccatgt gtgnttgcat gaggaactct ttagtggcag acacctaaga gacggctgcg    1560
gtcaccccac gcctccgtgg ctcaggagcc gtcctgggtg cataggacca gtttctgtga    1620
cttttctcca gttgggcatg ttgacagaca tgtttcccct cctccacccc tcattttctg    1680
gtcctcgcga ctgagagcca ggggcgacat catgaccttc tgtcccggcc gccttagccc    1740
cgggaacagg gaaggagct gggccgtttc tgtctgtgtc ccatcctgct gtccttctgt    1800
cctggatgtt tcatgggccc ggggcccccc agggaagctt acccctcctg tgctgggtgg    1860
aggccacggg acacctcagg tgccacccac cttggcccta aaacagccac caggaaagca    1920
gccggagagc cggacagcgg gcagcctgtc tgggttcctg aggcctgggg gtggcagacg    1980
aacccacggc gccgtggtcc cagcagcagg gttgtcagtc ggagcatcct ggggctccct    2040
ggctcctggc cgtctgtgag gtaggngcag taccgtgtat cgtaggtagc agtaggaacg    2100
ggggccaccg cggccctgca gccgttcatg gcggtgaggt gtgtgccaag cccacccggg    2160
gtgcagggcg tgacgtgtgg ggaataaata ggcgttgtga cctcaaaaaa aaaaaaaaaa    2220
a                                                                    2221
```

<210> SEQ ID NO 2
<211> LENGTH: 382
<212> TYPE: PRT
<213> ORGANISM: Homo sapiens

<400> SEQUENCE: 2

Met Asp Asn Lys Lys Arg Leu Ala Tyr Ala Ile Ile Gln Phe Leu His
 1               5                  10                  15

```
Asp Gln Leu Arg His Gly Gly Leu Ser Ser Asp Ala Gln Glu Ser Leu
            20                  25                  30
Glu Val Ala Ile Gln Cys Leu Glu Thr Ala Phe Gly Val Thr Val Glu
         35                  40                  45
Asp Ser Asp Leu Ala Leu Pro Gln Thr Leu Pro Glu Ile Phe Glu Ala
         50                  55                  60
Ala Ala Thr Gly Lys Glu Met Pro Gln Asp Leu Arg Ser Pro Ala Arg
 65                  70                  75                  80
Thr Pro Pro Ser Glu Glu Asp Ser Ala Glu Ala Glu Arg Leu Lys Thr
                 85                  90                  95
Glu Gly Asn Glu Gln Met Lys Val Glu Asn Phe Glu Ala Ala Val His
            100                 105                 110
Phe Tyr Gly Lys Ala Ile Glu Leu Asn Pro Ala Asn Ala Val Tyr Phe
            115                 120                 125
Cys Asn Arg Ala Ala Ala Tyr Ser Lys Leu Gly Asn Tyr Ala Gly Ala
        130                 135                 140
Val Gln Asp Cys Glu Arg Ala Ile Cys Ile Asp Pro Ala Tyr Ser Lys
145                 150                 155                 160
Ala Tyr Gly Arg Met Gly Leu Ala Leu Ser Ser Leu Asn Lys His Val
                165                 170                 175
Glu Ala Val Ala Tyr Tyr Lys Lys Ala Leu Glu Leu Asp Pro Asp Asn
            180                 185                 190
Glu Thr Tyr Lys Ser Asn Leu Lys Ile Ala Glu Leu Lys Leu Arg Glu
            195                 200                 205
Ala Pro Ser Pro Thr Gly Gly Val Gly Ser Phe Asp Ile Ala Gly Leu
        210                 215                 220
Leu Asn Asn Pro Gly Phe Met Ser Met Ala Ser Asn Leu Met Asn Asn
225                 230                 235                 240
Pro Gln Ile Gln Gln Leu Met Ser Gly Met Ile Ser Gly Gly Asn Asn
                245                 250                 255
Pro Leu Gly Thr Pro Gly Thr Ser Pro Ser Gln Asn Asp Leu Ala Ser
            260                 265                 270
Leu Ile Gln Ala Gly Gln Gln Phe Ala Gln Gln Met Gln Gln Gln Asn
            275                 280                 285
Pro Glu Leu Ile Glu Gln Leu Arg Ser Gln Ser Gly Val Gly Arg Pro
        290                 295                 300
Ala Pro Ala Thr Thr Thr Ser Arg Ser Asp Ala Ala Cys Ser Arg Cys
305                 310                 315                 320
Asp Arg Val Leu Pro Trp Pro Thr Arg Arg Lys Pro Ser Gly Cys Leu
                325                 330                 335
Pro Leu Pro Pro Val Gly Leu Pro Glu Arg Gly Glu Glu Arg Asp Leu
            340                 345                 350
Gly Pro Ala Cys Gln Asp Gly Phe Ser Pro Phe Ile Ser Ala Leu Leu
        355                 360                 365
His Ser Leu Phe Val Thr Pro Leu Gln Pro Pro Asp Pro Ser
        370                 375                 380

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 3
```

```
agtagtacat catatgcaac cta                                              23

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 4
tccacacagg atccccataa t                                                21

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 5
cgggatccgg tgcgagagcg tcggtattaa g                                     31

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 6
gctctagacc tgtatctaat agagcttc                                         28

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 7
ggccagatga gagaaccaag g                                                21

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 8
caaagagtga cttaagggaa gctaaag                                          27

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 9
```

```
cctatagctt tatgtccgca g                                          21
```

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 10

```
ctttagcttc ccttaagtca ctctttg                                    27
```

<210> SEQ ID NO 11
<211> LENGTH: 34
<212> TYPE: PRT
<213> ORGANISM: Artificial Sequence
<220> FEATURE:
<223> OTHER INFORMATION: Description of Artificial Sequence:TPR Motifs
      Consensus Sequence
<220> FEATURE:
<221> NAME/KEY: UNSURE
<222> LOCATION: (1)
<223> OTHER INFORMATION: Can be any large hydrophobic amino acid.
<220> FEATURE:
<221> NAME/KEY: UNSURE
<222> LOCATION: (2)..(3)
<223> OTHER INFORMATION: Can be any amino acid.
<220> FEATURE:
<221> NAME/KEY: UNSURE
<222> LOCATION: (4)
<223> OTHER INFORMATION: Can be any large hydrophobic amino acid.
<220> FEATURE:
<221> NAME/KEY: VARIANT
<222> LOCATION: (5)
<223> OTHER INFORMATION: Can be an Alanine as well.
<220> FEATURE:
<221> NAME/KEY: UNSURE
<222> LOCATION: (6)
<223> OTHER INFORMATION: Can be any amino acid.
<220> FEATURE:
<221> NAME/KEY: UNSURE
<222> LOCATION: (7)
<223> OTHER INFORMATION: Can be any large hydrophobic amino acid.
<220> FEATURE:
<221> NAME/KEY: VARIANT
<222> LOCATION: (8)
<223> OTHER INFORMATION: Can be a Phenylalanine as well.
<220> FEATURE:
<221> NAME/KEY: UNSURE
<222> LOCATION: (9)..(13)
<223> OTHER INFORMATION: Can be any amino acid.
<220> FEATURE:
<221> NAME/KEY: UNSURE
<222> LOCATION: (14)
<223> OTHER INFORMATION: Can be any large hydrophobic amino acid.
<220> FEATURE:
<221> NAME/KEY: UNSURE
<222> LOCATION: (15)..(16)
<223> OTHER INFORMATION: Can be any amino acid.
<220> FEATURE:
<221> NAME/KEY: UNSURE
<222> LOCATION: (18)
<223> OTHER INFORMATION: Can be any large hydrophobic amino acid.
<220> FEATURE:
<221> NAME/KEY: UNSURE
<222> LOCATION: (19)..(20)
<223> OTHER INFORMATION: Can be any amino acid.
<220> FEATURE:
<221> NAME/KEY: VARIANT
<222> LOCATION: (21)
<223> OTHER INFORMATION: Can be Tyrosine as well.
<220> FEATURE:
<221> NAME/KEY: UNSURE
<222> LOCATION: (22)..(23)
<223> OTHER INFORMATION: Can be any amino acid.

-continued

```
<220> FEATURE:
<221> NAME/KEY: UNSURE
<222> LOCATION: (25)
<223> OTHER INFORMATION: Can be any large hydrophobic amino acid.
<220> FEATURE:
<221> NAME/KEY: UNSURE
<222> LOCATION: (26)
<223> OTHER INFORMATION: Can be any amino acid.
<220> FEATURE:
<221> NAME/KEY: UNSURE
<222> LOCATION: (27)
<223> OTHER INFORMATION: Can be any large hydrophobic amino acid.
<220> FEATURE:
<221> NAME/KEY: UNSURE
<222> LOCATION: (28)
<223> OTHER INFORMATION: Can be any amino acid.
<220> FEATURE:
<221> NAME/KEY: UNSURE
<222> LOCATION: (30)..(34)
<223> OTHER INFORMATION: Can be any amino acid.

<400> SEQUENCE: 11

Xaa Xaa Xaa Xaa Gly Xaa Xaa Tyr Xaa Xaa Xaa Xaa Xaa Xaa Xaa
 1               5                  10                  15

Ala Xaa Xaa Xaa Phe Xaa Xaa Ala Xaa Xaa Xaa Pro Xaa Xaa Xaa
                20                  25                  30

Xaa Xaa

<210> SEQ ID NO 12
<211> LENGTH: 34
<212> TYPE: PRT
<213> ORGANISM: Human Immunodeficiency Virus Type 1
<220> FEATURE:
<221> NAME/KEY: PEPTIDE
<222> LOCATION: (1)..(34)
<223> OTHER INFORMATION: TPR1

<400> SEQUENCE: 12

Leu Arg His Gly Gly Leu Ser Ser Asp Ala Gln Glu Ser Leu Glu Val
 1               5                  10                  15

Ala Ile Gln Cys Leu Glu Thr Ala Phe Gly Val Thr Val Glu Asp Ser
                20                  25                  30

Asp Leu

<210> SEQ ID NO 13
<211> LENGTH: 34
<212> TYPE: PRT
<213> ORGANISM: C. elegans
<220> FEATURE:
<221> NAME/KEY: PEPTIDE
<222> LOCATION: (1)..(34)
<223> OTHER INFORMATION: TPR1

<400> SEQUENCE: 13

Val Ser Gln Asn Gln Ala Thr Ala Glu Gln Ala Glu Ala Leu Glu Val
 1               5                  10                  15

Ala Ile Gln Cys Leu Glu His Ser Phe Gly Leu Asp Asp Ala Ser Tyr
                20                  25                  30

Ala Phe

<210> SEQ ID NO 14
<211> LENGTH: 34
<212> TYPE: PRT
<213> ORGANISM: S. cerevisiae
<220> FEATURE:
<221> NAME/KEY: PEPTIDE
<222> LOCATION: (1)..(34)
```

<223> OTHER INFORMATION: TPR1

<400> SEQUENCE: 14

Val Glu Lys Lys Glu Ile Ser Glu Asp Gly Ala Asp Ser Leu Asn Val
 1               5                  10                  15

Ala Met Asp Cys Ile Ser Glu Ala Phe Gly Phe Glu Arg Glu Ala Val
             20                  25                  30

Ser Gly

<210> SEQ ID NO 15
<211> LENGTH: 34
<212> TYPE: PRT
<213> ORGANISM: Human Immunodeficiency Virus Type 1
<220> FEATURE:
<221> NAME/KEY: PEPTIDE
<222> LOCATION: (1)..(34)
<223> OTHER INFORMATION: TPR2

<400> SEQUENCE: 15

Leu Lys Thr Glu Gly Asn Glu Gln Met Lys Val Glu Asn Phe Glu Ala
 1               5                  10                  15

Ala Val His Phe Tyr Gly Lys Ala Ile Glu Leu Asn Pro Ala Asn Ala
             20                  25                  30

Val Tyr

<210> SEQ ID NO 16
<211> LENGTH: 33
<212> TYPE: PRT
<213> ORGANISM: C. elegans
<220> FEATURE:
<221> NAME/KEY: PEPTIDE
<222> LOCATION: (1)..(33)
<223> OTHER INFORMATION: TPR2

<400> SEQUENCE: 16

Leu Lys Glu Glu Gly Asn Asp Leu Met Lys Ala Ser Gln Phe Glu Ala
 1               5                  10                  15

Ala Val Gln Lys Tyr Asn Ala Ala Ile Lys Leu Asn Arg Asp Pro Val
             20                  25                  30

Tyr

<210> SEQ ID NO 17
<211> LENGTH: 34
<212> TYPE: PRT
<213> ORGANISM: S. cerevisiae
<220> FEATURE:
<221> NAME/KEY: PEPTIDE
<222> LOCATION: (1)..(34)
<223> OTHER INFORMATION: TPR2

<400> SEQUENCE: 17

Leu Lys Met Gln Gly Asn Lys Ala Met Ala Asn Lys Asp Tyr Glu Leu
 1               5                  10                  15

Ala Ile Asn Lys Tyr Thr Glu Ala Ile Lys Val Leu Pro Thr Asn Ala
             20                  25                  30

Ile Tyr

<210> SEQ ID NO 18
<211> LENGTH: 34
<212> TYPE: PRT
<213> ORGANISM: Homo sapiens
<220> FEATURE:
<221> NAME/KEY: PEPTIDE

```
<222> LOCATION: (1)..(34)
<223> OTHER INFORMATION: TPR1

<400> SEQUENCE: 18
```

Leu Lys Thr Gln Ala Asn Asp Tyr Phe Lys Ala Lys Asp Tyr Glu Asn
 1               5                   10                  15

Ala Ile Lys Phe Tyr Ser Gln Ala Ile Glu Leu Asn Pro Ser Asn Ala
                20                  25                  30

Ile Tyr

```
<210> SEQ ID NO 19
<211> LENGTH: 34
<212> TYPE: PRT
<213> ORGANISM: Homo sapiens
<220> FEATURE:
<221> NAME/KEY: PEPTIDE
<222> LOCATION: (1)..(34)
<223> OTHER INFORMATION: TPR1

<400> SEQUENCE: 19
```

Leu Lys Asn Ile Gly Asn Thr Phe Phe Lys Ser Gln Asn Trp Glu Met
 1               5                   10                  15

Ala Ile Lys Lys Tyr Ala Glu Val Leu Arg Tyr Val Asp Ser Ser Lys
                20                  25                  30

Ala Val

```
<210> SEQ ID NO 20
<211> LENGTH: 34
<212> TYPE: PRT
<213> ORGANISM: Homo sapiens
<220> FEATURE:
<221> NAME/KEY: PEPTIDE
<222> LOCATION: (1)..(34)
<223> OTHER INFORMATION: TPR3

<400> SEQUENCE: 20
```

Phe Cys Asn Arg Ala Ala Ala Tyr Ser Lys Leu Gly Asn Tyr Ala Gly
 1               5                   10                  15

Ala Val Gln Asp Cys Glu Arg Ala Ile Cys Ile Asp Pro Ala Tyr Ser
                20                  25                  30

Lys Ala

```
<210> SEQ ID NO 21
<211> LENGTH: 34
<212> TYPE: PRT
<213> ORGANISM: Homo sapiens
<220> FEATURE:
<221> NAME/KEY: PEPTIDE
<222> LOCATION: (1)..(34)
<223> OTHER INFORMATION: TPR3

<400> SEQUENCE: 21
```

Phe Cys Asn Arg Ala Ala Ala Tyr Cys Arg Leu Glu Gln Tyr Asp Leu
 1               5                   10                  15

Ala Ile Gln Asp Cys Arg Thr Ala Leu Ala Leu Asp Pro Ser Tyr Ser
                20                  25                  30

Lys Ala

```
<210> SEQ ID NO 22
<211> LENGTH: 34
<212> TYPE: PRT
<213> ORGANISM: Homo sapiens
<220> FEATURE:
```

```
<221> NAME/KEY: PEPTIDE
<222> LOCATION: (1)..(34)
<223> OTHER INFORMATION: TPR3

<400> SEQUENCE: 22

Tyr Ala Asn Arg Ala Ala Ala His Ser Ser Leu Lys Glu Tyr Asp Gln
 1               5                  10                  15

Ala Val Lys Asp Ala Glu Ser Ala Ile Ser Ile Asp Pro Ser Tyr Phe
            20                  25                  30

Arg Gly

<210> SEQ ID NO 23
<211> LENGTH: 34
<212> TYPE: PRT
<213> ORGANISM: Homo sapiens
<220> FEATURE:
<221> NAME/KEY: PEPTIDE
<222> LOCATION: (1)..(34)
<223> OTHER INFORMATION: TPR2

<400> SEQUENCE: 23

Tyr Gly Asn Arg Ser Leu Ala Tyr Leu Arg Thr Glu Cys Tyr Gly Tyr
 1               5                  10                  15

Ala Leu Gly Asp Ala Thr Arg Ala Ile Glu Leu Asp Lys Lys Tyr Ile
            20                  25                  30

Lys Gly

<210> SEQ ID NO 24
<211> LENGTH: 34
<212> TYPE: PRT
<213> ORGANISM: Homo sapiens
<220> FEATURE:
<221> NAME/KEY: PEPTIDE
<222> LOCATION: (1)..(34)
<223> OTHER INFORMATION: TPR2

<400> SEQUENCE: 24

Val Leu Asn Ile Gly Ala Cys Lys Leu Lys Met Ser Asn Trp Gln Gly
 1               5                  10                  15

Ala Ile Asp Ser Cys Leu Glu Ala Leu Glu Leu Asp Pro Ser Asn Thr
            20                  25                  30

Lys Ala

<210> SEQ ID NO 25
<211> LENGTH: 34
<212> TYPE: PRT
<213> ORGANISM: Homo sapiens
<220> FEATURE:
<221> NAME/KEY: PEPTIDE
<222> LOCATION: (1)..(34)
<223> OTHER INFORMATION: TPR4

<400> SEQUENCE: 25

Tyr Gly Arg Met Gly Leu Ala Leu Ser Ser Leu Asn Lys His Val Glu
 1               5                  10                  15

Ala Val Ala Tyr Tyr Lys Lys Ala Leu Glu Leu Asp Pro Asp Asn Glu
            20                  25                  30

Thr Tyr

<210> SEQ ID NO 26
<211> LENGTH: 34
<212> TYPE: PRT
<213> ORGANISM: Homo sapiens
```

```
<220> FEATURE:
<221> NAME/KEY: PEPTIDE
<222> LOCATION: (1)..(34)
<223> OTHER INFORMATION: TPR4

<400> SEQUENCE: 26

Trp Gly Arg Met Gly Leu Ala Tyr Ser Cys Gln Asn Arg Tyr Glu His
 1               5                  10                  15
Ala Ala Glu Ala Tyr Lys Lys Ala Leu Glu Leu Glu Pro Asn Gln Glu
            20                  25                  30
Ser Tyr

<210> SEQ ID NO 27
<211> LENGTH: 34
<212> TYPE: PRT
<213> ORGANISM: Homo sapiens
<220> FEATURE:
<221> NAME/KEY: PEPTIDE
<222> LOCATION: (1)..(34)
<223> OTHER INFORMATION: TPR4

<400> SEQUENCE: 27

Tyr Ser Arg Leu Gly Phe Ala Lys Tyr Ala Gln Gly Lys Pro Glu Glu
 1               5                  10                  15
Ala Leu Glu Ala Tyr Lys Lys Val Leu Asp Ile Glu Gly Asp Asn Ala
            20                  25                  30
Thr Glu

<210> SEQ ID NO 28
<211> LENGTH: 34
<212> TYPE: PRT
<213> ORGANISM: Homo sapiens
<220> FEATURE:
<221> NAME/KEY: PEPTIDE
<222> LOCATION: (1)..(34)
<223> OTHER INFORMATION: TPR3

<400> SEQUENCE: 28

Tyr Tyr Arg Arg Ala Ala Ser Asn Met Ala Leu Gly Lys Phe Arg Ala
 1               5                  10                  15
Ala Leu Arg Asp Tyr Glu Thr Val Val Lys Val Lys Pro His Asp Lys
            20                  25                  30
Asp Ala

<210> SEQ ID NO 29
<211> LENGTH: 34
<212> TYPE: PRT
<213> ORGANISM: Homo sapiens
<220> FEATURE:
<221> NAME/KEY: PEPTIDE
<222> LOCATION: (1)..(34)
<223> OTHER INFORMATION: TPR3

<400> SEQUENCE: 29

Leu Tyr Arg Arg Ala Gln Gly Trp Gln Gly Leu Lys Glu Tyr Asp Gln
 1               5                  10                  15
Ala Leu Ala Asp Leu Lys Lys Ala Gln Gly Ile Ala Pro Glu Asp Lys
            20                  25                  30
Ala Ile
```